(12) United States Patent
Martineau et al.

(10) Patent No.: US 10,260,090 B2
(45) Date of Patent: Apr. 16, 2019

(54) ACCELERATED ISOTHERMAL AMPLIFICATION OF DNA

(71) Applicants: Rhett L. Martineau, Gilbert, AZ (US); Shih-hui Chao, Phoenix, AZ (US); Weimin Gao, Chandler, AZ (US); Shufang Ci, Tempe, AZ (US); Deirdre R. Meldrum, Phoenix, AZ (US)

(72) Inventors: Rhett L. Martineau, Gilbert, AZ (US); Shih-hui Chao, Phoenix, AZ (US); Weimin Gao, Chandler, AZ (US); Shufang Ci, Tempe, AZ (US); Deirdre R. Meldrum, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 3 days.

(21) Appl. No.: 15/213,194

(22) Filed: Jul. 18, 2016

(65) Prior Publication Data
US 2017/0107549 A1 Apr. 20, 2017

Related U.S. Application Data

(60) Provisional application No. 62/193,205, filed on Jul. 16, 2015.

(51) Int. Cl.
*C12P 19/34* (2006.01)
*C12Q 1/68* (2018.01)
*C12Q 1/6844* (2018.01)

(52) U.S. Cl.
CPC .................. *C12Q 1/6844* (2013.01)

(58) Field of Classification Search
CPC ............... C12Q 1/6844; C12Q 2525/161
See application file for complete search history.

(56) References Cited

U.S. PATENT DOCUMENTS

| | | | |
|---|---|---|---|
| 6,410,278 B1 | 6/2002 | Notomi | |
| 7,803,579 B2 | 9/2010 | Mitani et al. | |
| 2012/0157326 A1 | 6/2012 | Tisi et al. | |
| 2017/0107549 A1* | 4/2017 | Martineau ............ | C12P 19/34 |

OTHER PUBLICATIONS

Notomi et al. Loop-mediated Isothermal amplification of DNA, Nucleic Acids Research, (2000) vol. 28, No. 12.
Wang et al., Rapid and Sensitive Isothermal Detection of Nucleic-acid Sequence by Multiple Cross Displacement Amplification, Scientific Reports, Jul. 8, 2015, 5:11902, 16 pages.
Tanner et al., Simultaneous multiple target detection in real-time loop-mediated isothermal amplification., BioTechniques, Aug. 2012, 53(2):81-9.
Nagamine et al., Accelerated reaction by loop-mediated isothermal amplification using loop primers., Molecular and Cellular Probes, Jun. 2002, 16(3):223-9.
Surabattula et al., Simple, rapid, inexpensive platform for the diagnosis of malaria by loop mediated isothermal amplification (LAMP)., Experimental Parasitology, Jul. 2013, 134(3):333-40.
Suzuki et al., Heat denaturation increases the sensitivity of the cytomegalovirus loop-mediated isothermal amplification method., Microbiology and Immunology, Aug. 2010, 54(8):466-70.
Gandelman et al., Loop-mediated amplification accelerated by stem primers., International Journal of Molecular Sciences, 2011, 12(12):9108-24.
Kimura et al., Optimization of turn-back primers in isothermal amplification., Nucleic Acids Research, 2010, 39(9):e59(8 pages).
Mitani et al., Rapid SNP diagnostics using asymmetric isothermal amplification and a new mismatch-suppression technology., Nature Methods, Mar. 2007, 4(3):257-62.
Mori et al., Detection of Loop-Mediated Isothermal Amplification Reaction by Turbidity Derived from Magnesium Pyrophosphate Formation., Biochemical and Biophysical Research Communications, Nov. 2001, 289(1):150-4.
Mori et al., Real-time turbidimetry of LAMP reaction for quantifying template DNA., Journal of Biochemical and Biophysical Methods, May 2004, 59(2):145-57.
Njiru et al., Loop-Mediated Isothermal Amplification (LAMP) Method for Rapid Detection of Trypanosoma brucei rhodesiense., PLoS Neglected Tropical Diseases, Feb. 2002, 2(2):e147(8 pages).
Tomita et al., Loop-mediated isothermal amplification (LAMP) of gene sequences and simple visual detection of products., Nature Protocols, 2008, 3(5):877-82.
MacArthur et al., Global health diagnostics: research, development and regulation., Academy of Medical Sciences Workshop Report, Academy of Medical Sciences, Great Britain, Apr. 2009, 30 pages.
Geojith et al., Efficacy of loop mediated isothermal amplification (LAMP) assay for the laboratory identification of *Mycobacterium tuberculosis* isolates in a resource limited setting., Journal of Microbiological Methods, 2011, 84(1):71-3.
Poon et al., Sensitive and inexpensive molecular test for falciparum malaria: detecting Plasmodium falciparum DNA directly from heat-treated blood by loop-mediated isothermal amplification., Clinical Chemistry, Feb. 2006, 52(2):303-6.

(Continued)

*Primary Examiner* — David C Thomas
(74) *Attorney, Agent, or Firm* — Lee & Lin IP PLLC

(57) ABSTRACT

A method of synthesizing a nucleic acid complementary to a target nucleic acid sequence in a template nucleic acid includes annealing a swarm primer to a target nucleic acid, the swarm primer overlapping an F1 site of the target nucleic acid and extends toward the F2 site of the target nucleic acid. An inner primer may also be annealed to the target nucleic acid to produce a complimentary nucleic acid having a single-strand loop onto which further primers may anneal. A plurality of amplicons may be reproduced, many of which may have further primers annealed thereto to generate more complementary nucleic acids.

20 Claims, 40 Drawing Sheets

Specification includes a Sequence Listing.

(56) References Cited

OTHER PUBLICATIONS

Njiru et al., African trypanosomiasis: Sensitive and rapid detection of the sub-genus *Trypanozoon* by loop-mediated isothermal amplification (LAMP) of parasite DNA., International Journal for Parasitology, Apr. 2008, 38(5):589-99.
Curtis et al., Rapid detection of HIV-1 by reverse-transcription, loop-mediated isothermal amplification (RT-LAMP)., Journal of Virological Methods, Aug. 2008, 151(2):264-70.
Sattabongkot et al., Loop-mediated isothermal amplification assay for rapid diagnosis of malaria infections in an area of endemicity in Thailand., Journal of Clinical Microbiology, May 2014, 52(5):1471-7.
Francois et al., Robustness of a loop-mediated isothermal amplification reaction for diagnostic applications., FEMS Immunology & Medical Microbiology, 2011, 62(1):41-8.
Torres et al., LAVA: An Open-Source Approach to Designing LAMP (Loop-Mediated Isothermal Amplification) DNA Signatures., BMC Bioinformatics, 2011, 12:240:(7 pages).
Iseki et al., Development of a multiplex loop-mediated isothermal amplification (mLAMP) method for the simultaneous detection of bovine Babesia parasites., Journal of Microbiological Methods, Dec. 2007, 71(3):281-7.

\* cited by examiner

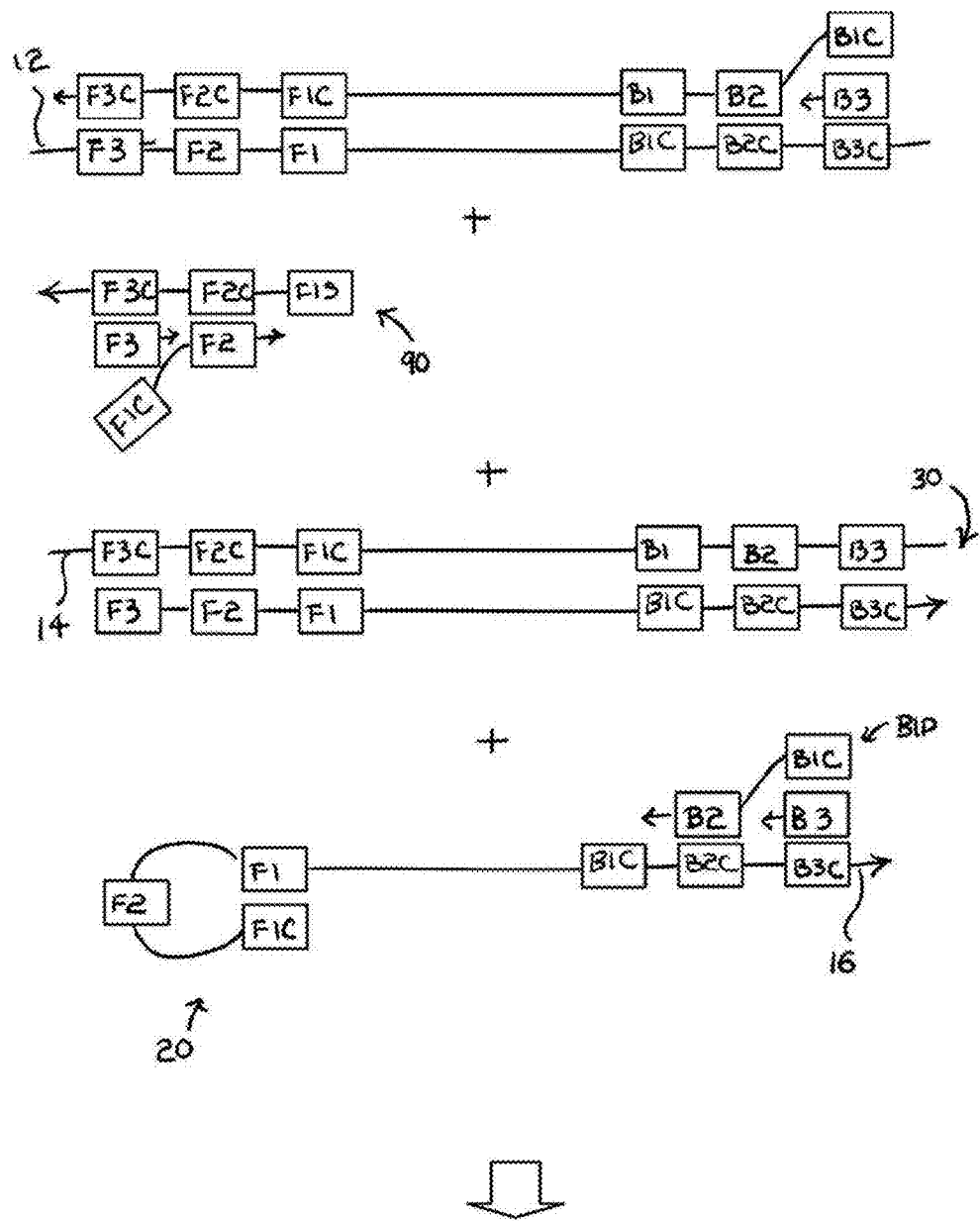

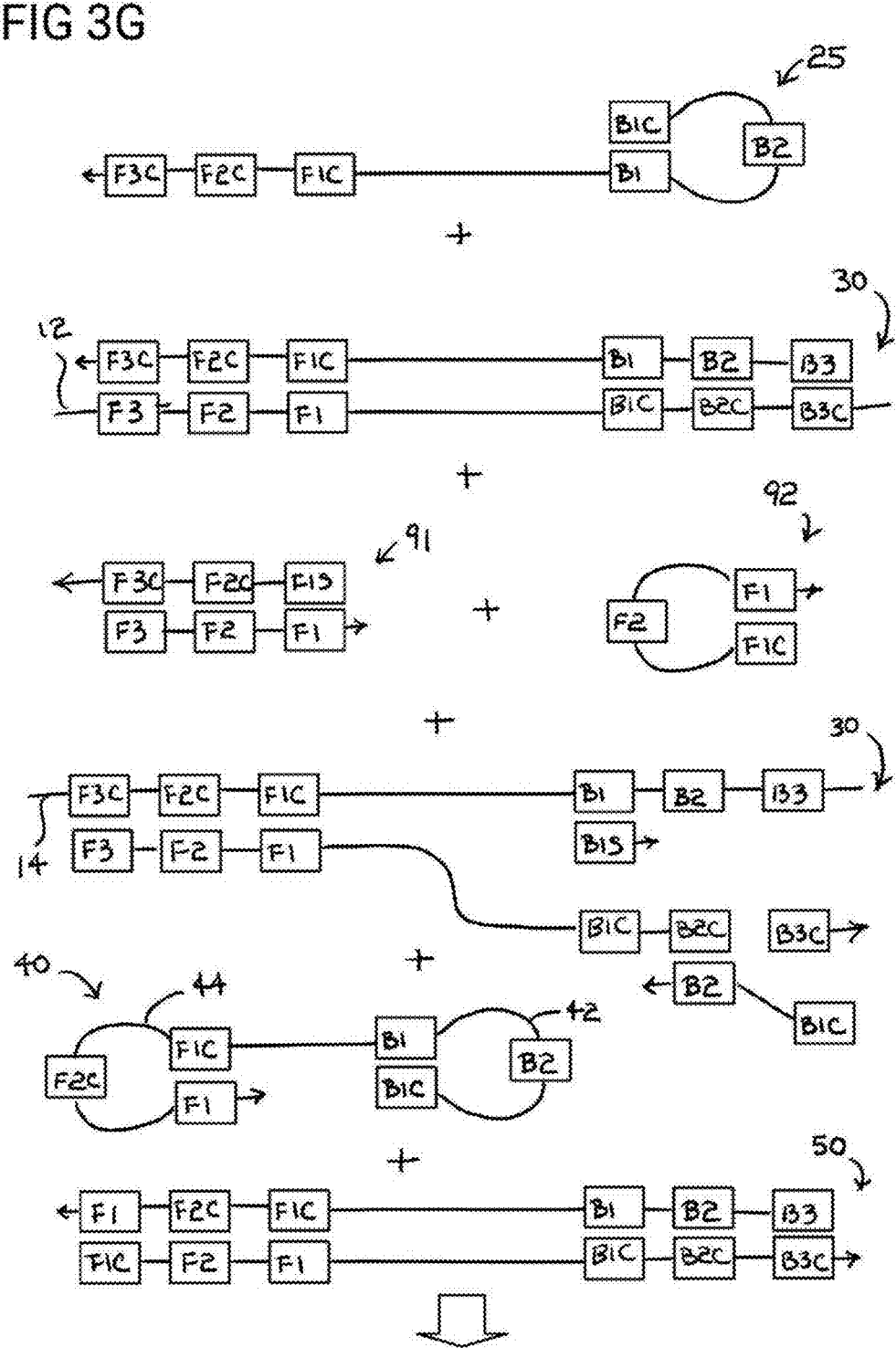

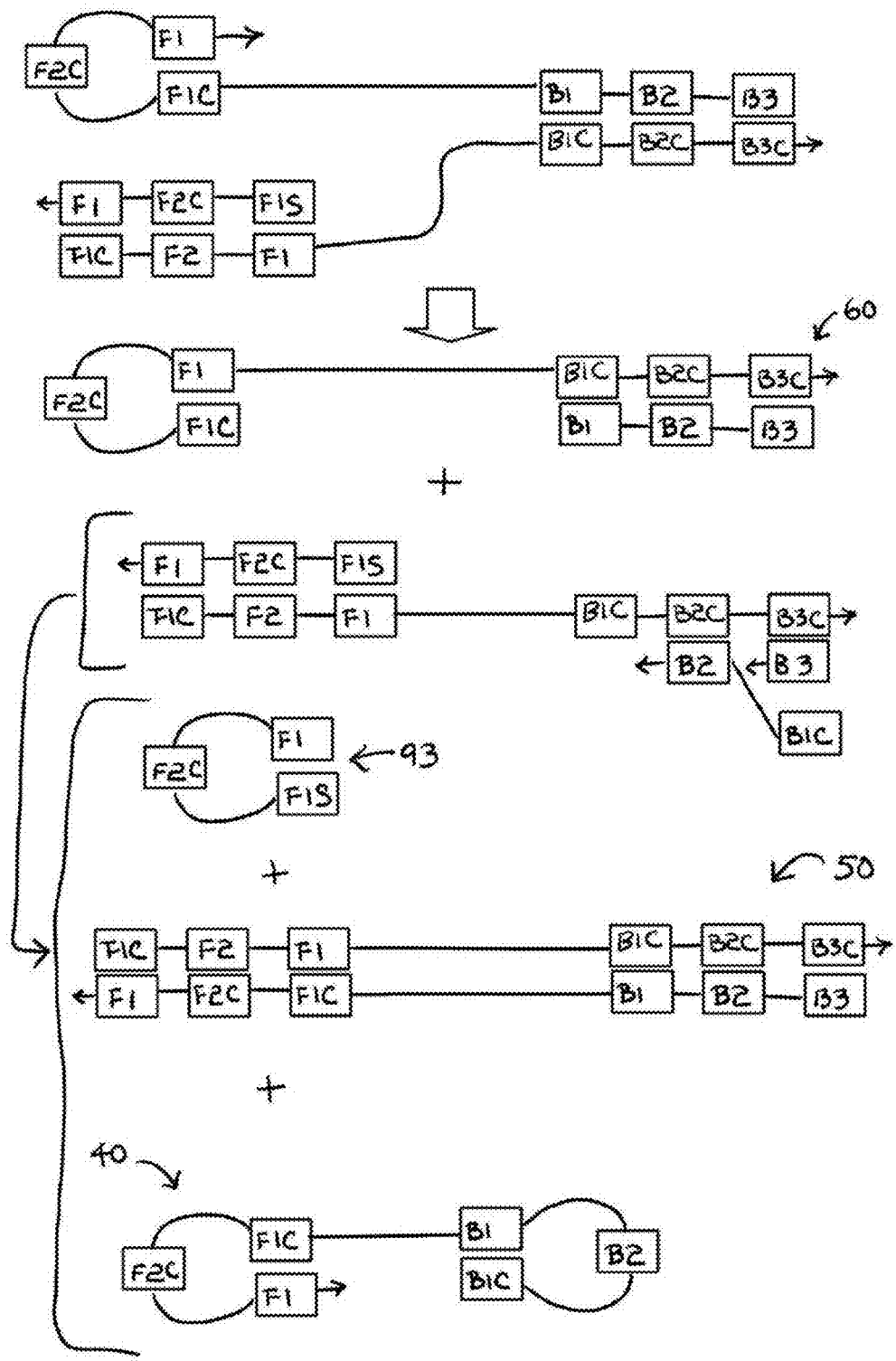

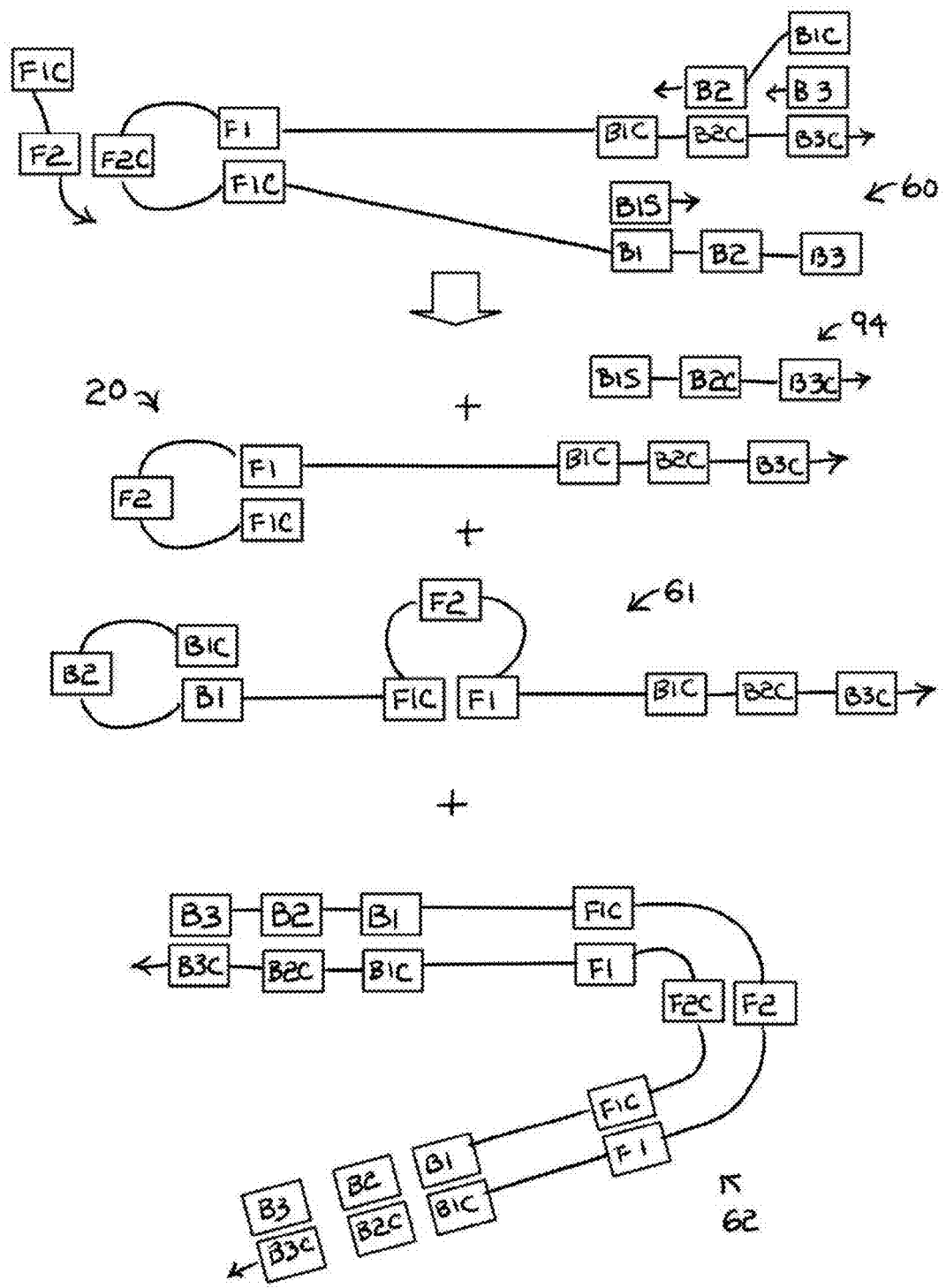

FIG 4C
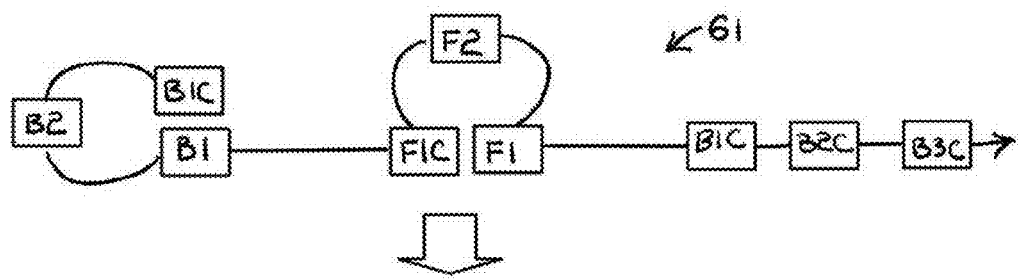
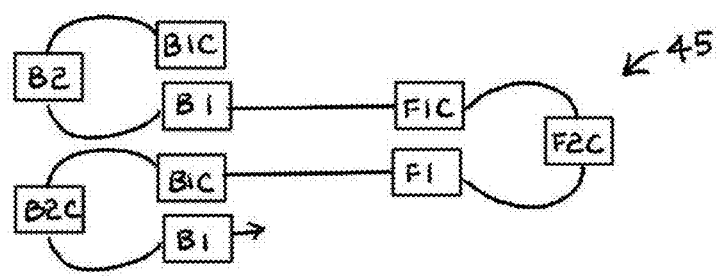
+
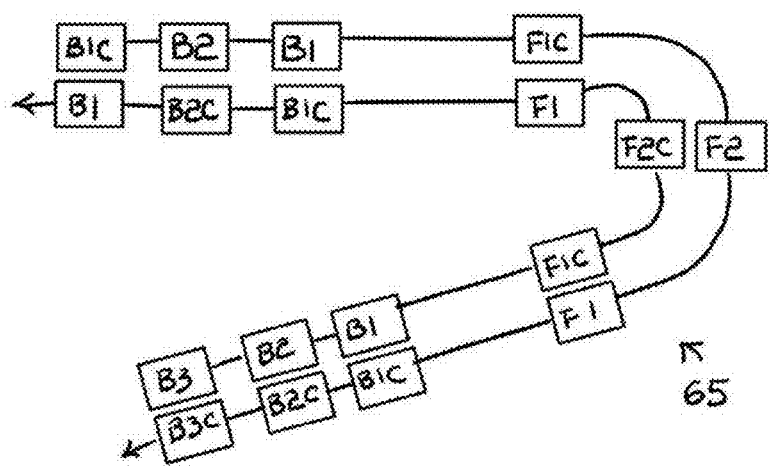

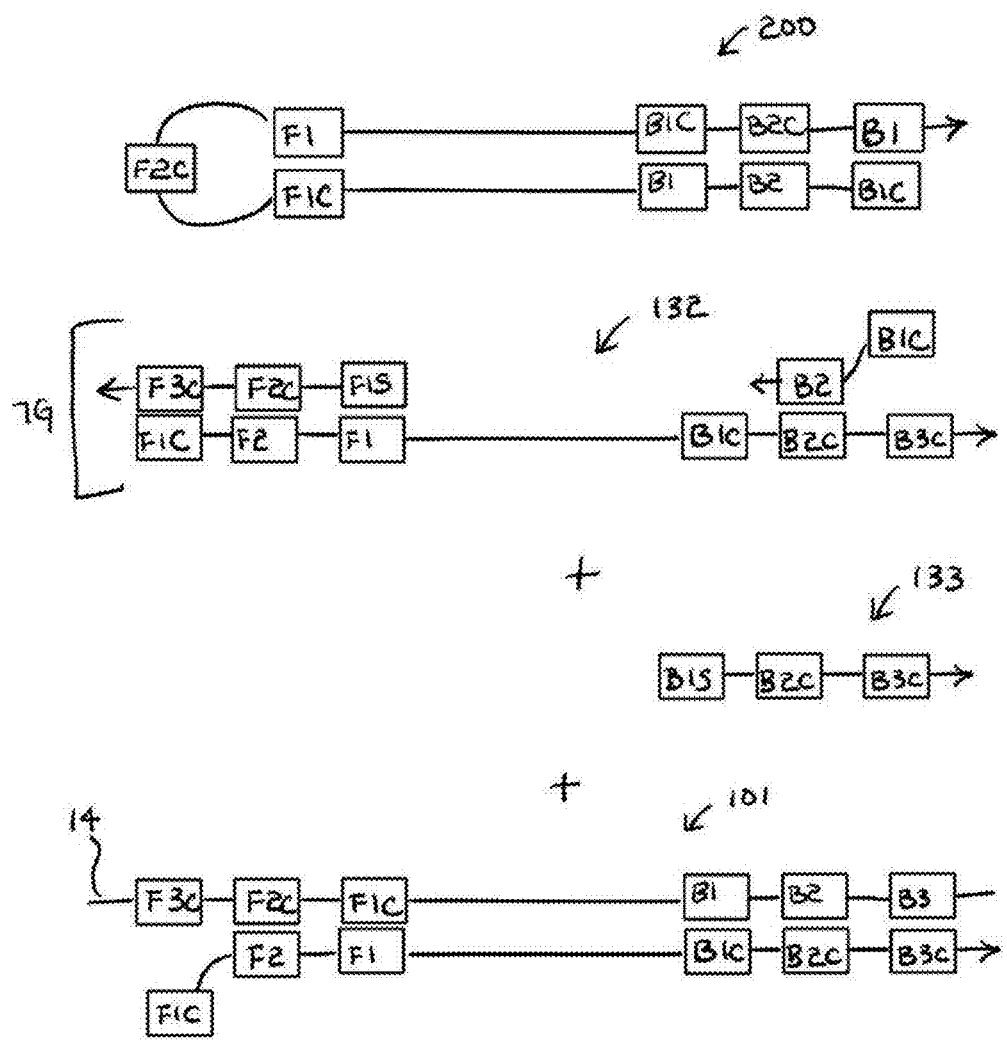

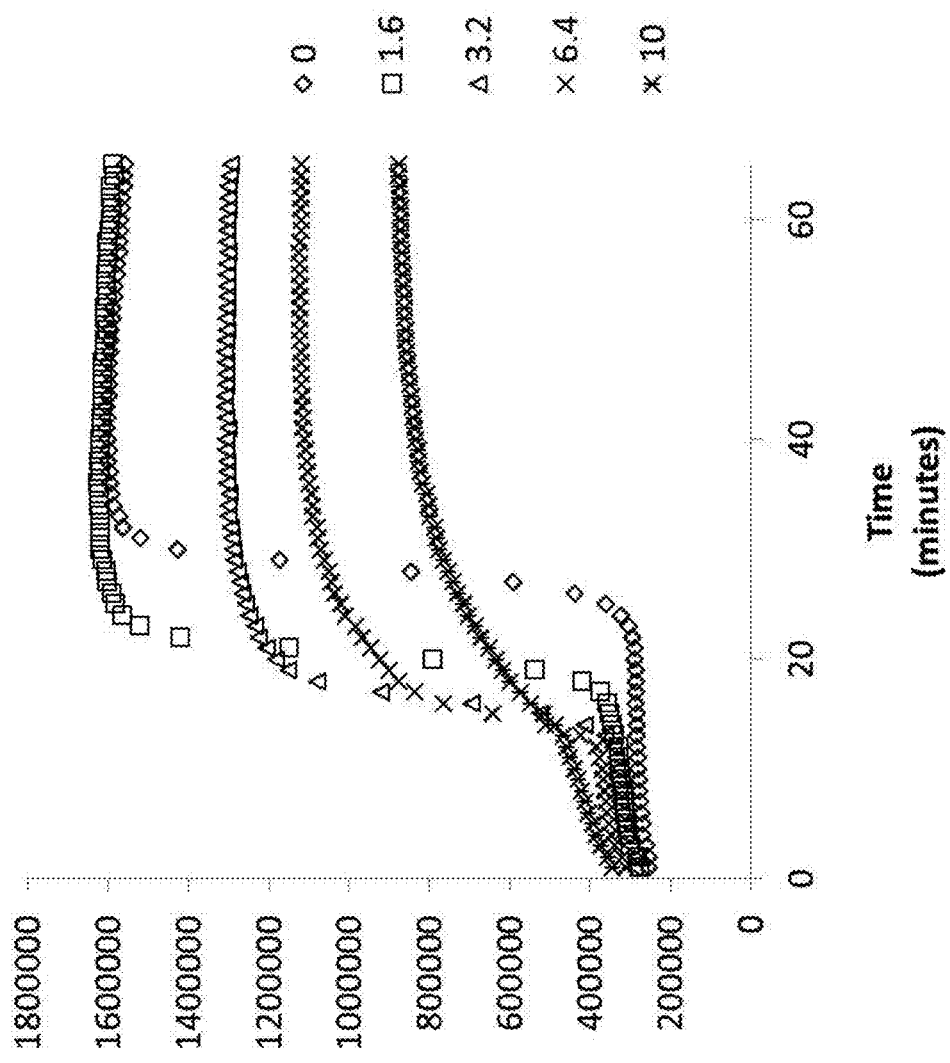
FIG 10 Increasing return on F1/B1S primer concentrations

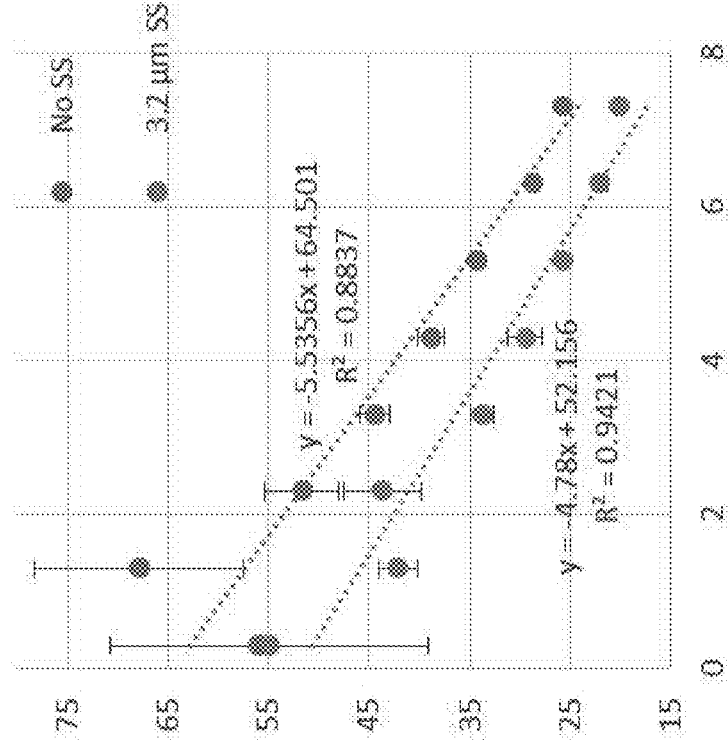
FIG. 12 - Performance of F1S/B1S effect on dose response curve with EvaGreen intercalating dye
'SS' indicates F1S/B1S primers. Concentration is in micromoles (μM).

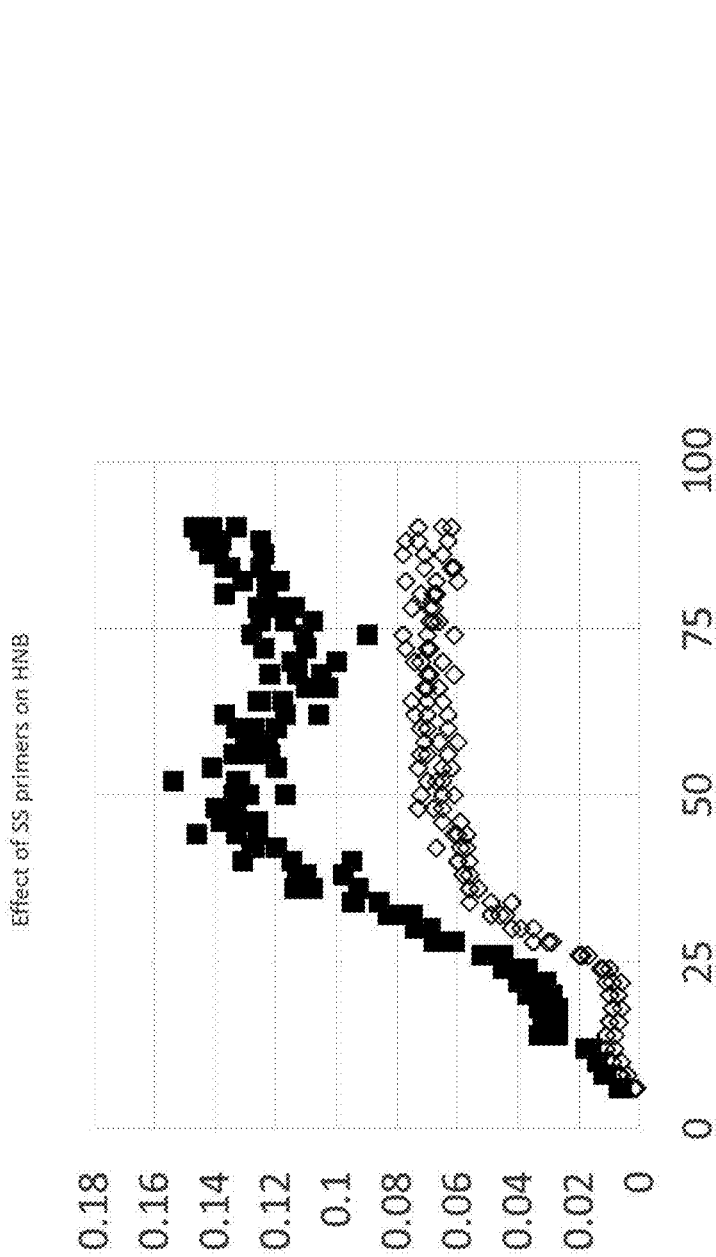
FIG.13A – Increased signal production in Hydroxynaphthol blue solution due to Swarm primers
Swarm primers are graphed as black squares; reactions without Swarm primers are open diamonds. 3.2 µM Swarm concentration used in Hydroxynaphthol blue solution.

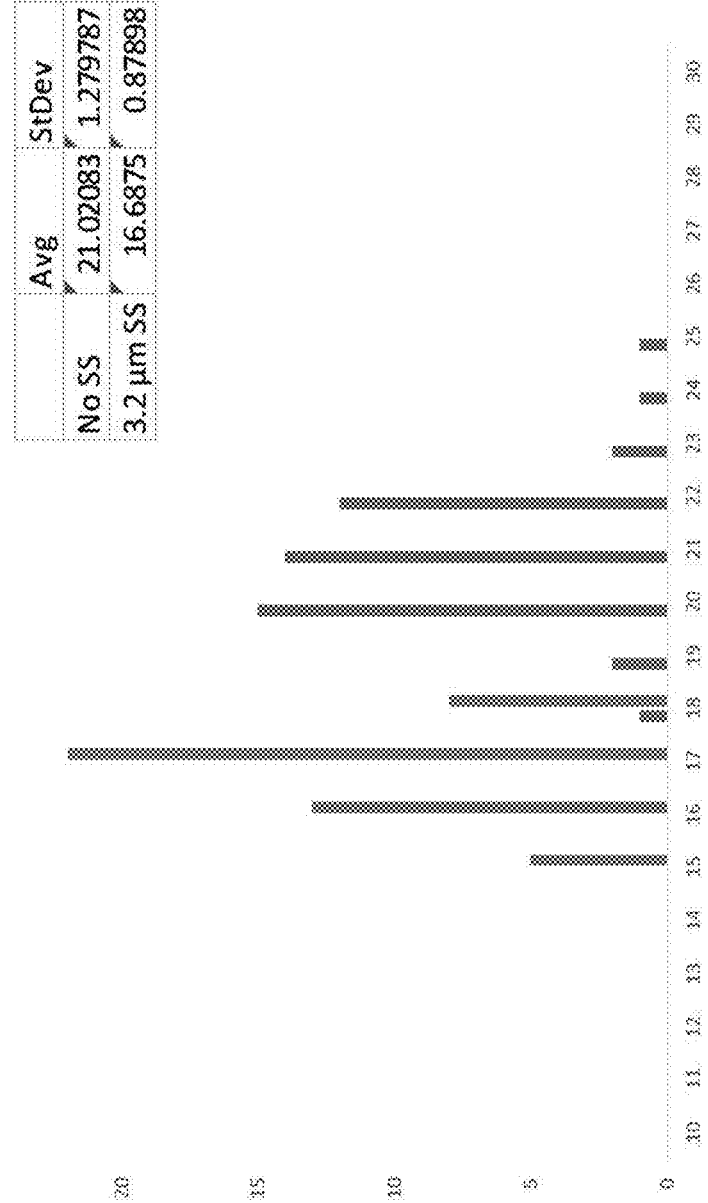
FIG. 13B - Reduced variability associated with Swarm primers

FIG. 17 FIP/BIP, F3/B3, LF/LB with/without F1S/B1S performance comparison

Top is with F1S/B1S, bottom is without. These graphs show the derivative of fluorescence production data. No heat denaturation in either case. With F1S, B1S, rate of reaction is increased, and lower concentrations are detected.

FIG. 18

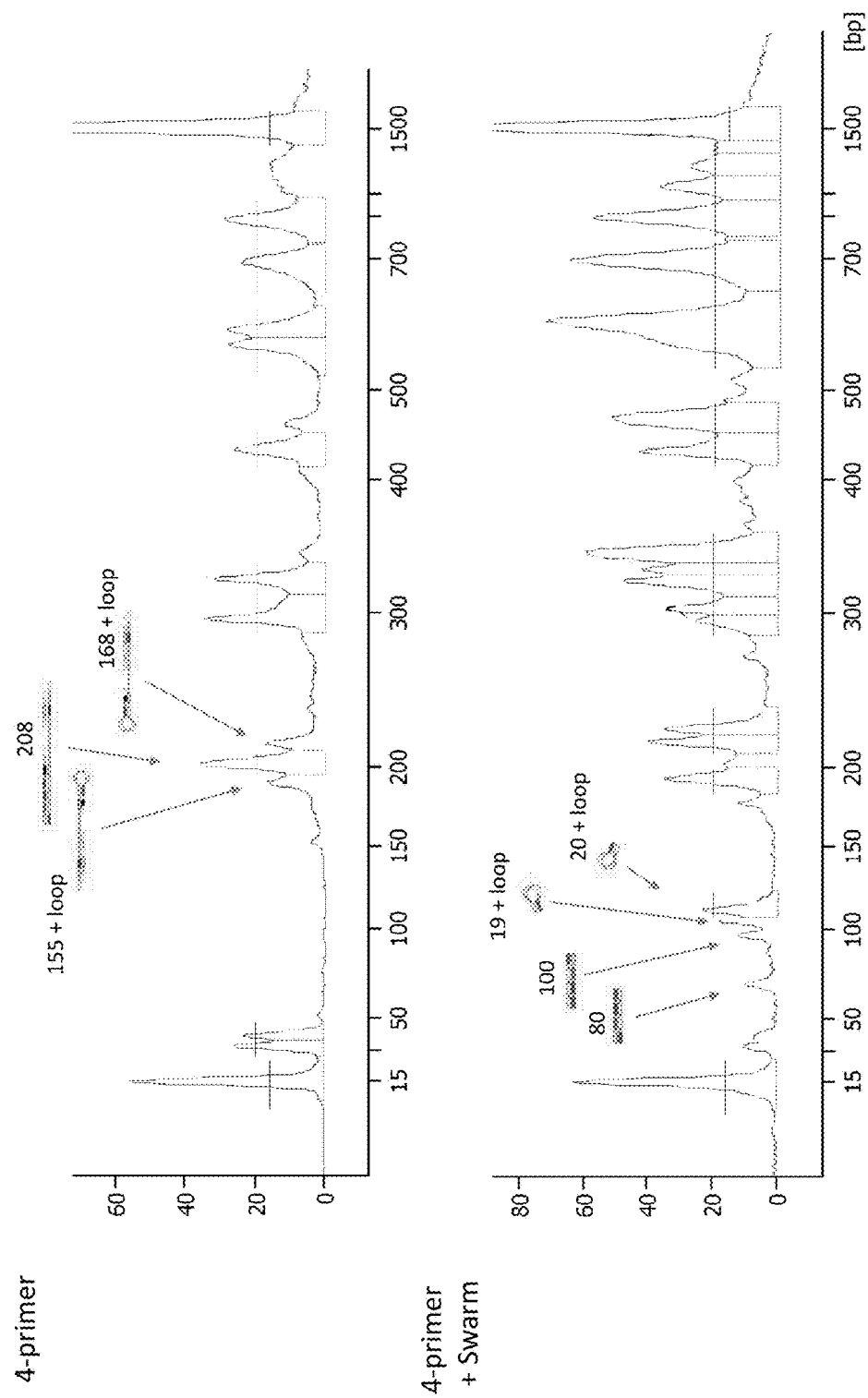

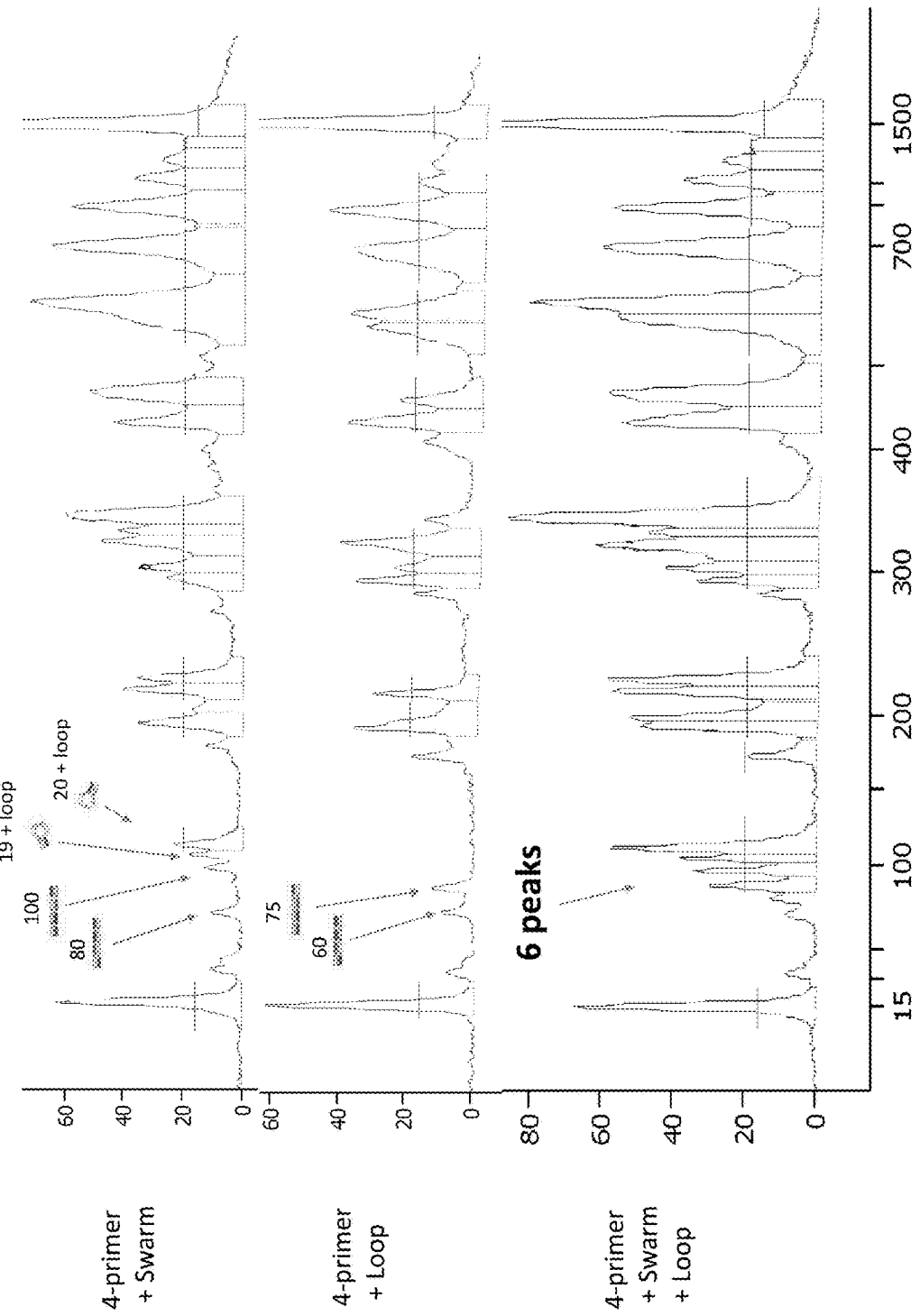

ACCELERATED ISOTHERMAL AMPLIFICATION OF DNA

FIELD OF INVENTION

The invention is related to a method of synthesizing nucleic acid composed of a specific nucleotide sequence and a method of amplifying nucleic acid.

BACKGROUND OF THE INVENTION

The invention relates generally to the amplification of polynucleic acids, more particularly isothermal amplification of double-stranded DNA or RNA. More specifically, the invention relates to improvements to the loop-mediated isothermal amplification (LAMP) reaction, wherein minute amounts of DNA can be quantified using relatively inexpensive equipment without temperature cycling or the addition of successive reagents.

Various techniques exist that help speed up the amplification of nucleic acid to aid research. The polymerase chain reaction (PCR) is one of such techniques used to amplify DNA to generate many orders of magnitude copies of the sequence of interest. To initiate PCR, the two strands of the DNA are first separated into single strands during a denaturation step. This step is often achieved by breaking the hydrogen bonds between the two strands using high temperature (94-98° C.). Once the two strands are separated, temperature is lowered to between 50-60° C. so that primers may anneal to each of the single strands. Controlling the temperature is critical because the temperature must be low enough to allow hybridization between the primer and the strand to take place, but high enough for specificity so that hybridization will not occur unless the primer is perfectly complementary to the targeted sequence on the strand. DNA polymerase then binds to the primer-strand and begins DNA extension, creating a new strand with a sequence that is complementary to the single-strand serving as its template. Depending on the specific DNA polymerase used, the temperature during this extension step is typically increased to between 70-80° C. again to optimize the reaction.

This cycle of denaturation, annealing and extension are repeated until the desired order of magnitude of DNA fragments is made. With each cycle, the volume of DNA target is doubled, as each newly synthesized amplicon becomes another template after the denaturation step.

One drawback of PCR is the reliance on thermal cycling, which requires the use of precision cyclers to heat and cool the reaction to achieve the required temperatures of various steps of PCR.

Another technique for DNA amplification is loop-mediated isothermal amplification (LAMP). The LAMP method involves two specifically designed inner primers and two specifically designed outer (displacement) primers, targeting a total of six sequences, and a DNA polymerase with high strand displacement activity.

As shown in FIG. 1 (Notomi et al. Loop-mediated isothermal amplification of DNA, Nucleic Acids Research, (2000) Vol 28., No. 12), the sequences inside both ends of the target region for amplification are designated F2c and B2. Sequences outside the ends of F2c and B2 are designated F3c and B3, respectively; while the inner sequences from the ends of F2c and B2 are designated F1c and B1, respectively. In order to target the desired sequence for amplification, the forward inner primer (FIP) is specifically designed to include F1c and F2, which is complementary F2c. Similarly, the backward inner primer (BIP) is specifically designed to include B2 and B1c.

To start LAMP, targeted DNA and the four primers are heated to cause the double-stranded DNA to denature into single strands of DNA. The FIP hybridizes to F2c in the targeted single-stranded DNA and initiates DNA synthesis. Typically, primer F3 is added in lower concentration than FIP. F3 hybridizes to F3c (just outside of the F2c sequences) and begins DNA synthesis and displaces the FIP linked complementary strand that was initiated by the hybridization of F2c to F2. This displaced single strand forms a loop at one end, hybridizing F1c of the FIP to F1 region of the synthesized amplicon. This single loop amplicon serves as the template for BIP-initiated DNA amplification. Primer B3 then hybridizes and initiates strand displacement DNA synthesis, releasing the BIP-linked complementary strand created, leading to the production of a dumbbell form amplicon having two loops, one at each end of the amplicon. This dumbbell form amplicon structure is quickly converted to a stem-loop amplicon by self-primed DNA synthesis (structure 7). This stem-loop amplicon then serves as the starting material for LAMP cycling.

To initiate LAMP cycling, FIP anneals to the single-stranded region in the loop in the stem-loop amplicon (structure 7) and primes strand displacement DNA synthesis, releasing the previously synthesized strand. An intermediate one gapped stem-loop DNA with an additional inverted copy of the target sequence in the stem and a loop formed at the opposite end via the BIP sequence (structure 8) are produced. Subsequent self-primed strand displacement DNA synthesis yields one complementary structure of the original stem-loop amplicon (structure 10) and one gap repaired stem-loop amplicon with a stem elongated to twice as long (double copies of the target sequence) and a loop at the opposite end (structure 9). Both of these products then serve as template for a BIP-primed strand displacement reaction in the subsequent cycles. The final products are a mixture of stem-loop amplicons with various stem lengths and cauliflower-like structures with multiple loops formed by annealing between alternately inverted repeats of the target sequence in the same strand.

To accelerate LAMP, loop primers may be optionally used. The loop primer is designed to anneal to binding sites in the single-stranded loop region, either between B1 and B2 regions or between F1 and F2 regions on the amplicons. Without loop primers, LAMP cycling occurs with FIP and BIP initiating DNA synthesis only at sites F2c or B2c. With the addition of loop primers, loops including F2 and B2 sites are also used for further DNA synthesis, thereby increasing the speed and efficiency of amplification.

LAMP may also be accelerated by the use of stem primers. Stem primers target the stem portion of the stem-loop amplicon and do not bind to the single-stranded DNA loops. Stem primers are designed to target specific sequences between B1 and F1c, and F1 and B1c. These areas are theorized to be transiently single-stranded during early stages of amplicon formation, and thus stem primers have been theorized to be helpful in speeding up LAMP reactions since they target single-stranded regions to form new amplicons. Multiple stem primer sets may be designed for longer stems.

The mechanism of stem-accelerated LAMP is similar to LAMP in that the annealing and extension of FIP/BIP primer cause the displacement and release of the opposite strand. This released single strand provides a binding site for the stem primer even before the loops are formed to provide binding sites for loop primers. The stem primer hybridizes to the single strand and initiates DNA synthesis and the displacement of the FIP/BIP-initiated amplicon, producing another amplicon that may serve as a template. Theoretically, both stem primers and loop primers may be used in a single amplification. In reality, however, it may be difficult to find ten binding sites available on the targeted sequence.

Unlike PCR, the reactions of the steps involved in LAMP and stem-accelerated LAMP are carried out in reaction mixtures maintained at a constant temperature. Stem-accelerated LAMP may have advantages over LAMP, as stem primers offer more flexibility and less restriction. Stem primers also do not require to be designed with a specific orientation, while LAMP primers do. Stem-accelerated LAMP may also be carried out without displacement primers, which may be especially useful if the targeted sequence is short and cannot accommodate all eight binding sites.

Whereas LAMP provides a significant advantage over other methods of DNA amplification, it has drawbacks as well. LAMP generally requires pre-amplification heat or chemical denaturation, and has moderate reaction variability, which increases with lower template concentration reactions. LAMP also has moderate reaction speed, and whereas the results are generally detectable by the naked eye, LAMP provides relatively weak color/turbidity changes. Furthermore, since the primer system is complex, conventionally requiring four to six primers targeting six to eight distinct regions in the target DNA, it may be difficult to design high-performance primer sets to amplify a desired target sequence.

Accordingly, it is desirable to provide an improved system and method for DNA amplification that overcomes drawbacks and inadequacies of known methods and systems.

SUMMARY OF THE INVENTIONS

Generally speaking, in accordance with an embodiment of the invention, an improved isothermal amplification of double-stranded DNA or RNA is provided. For the sake of simplicity, the term "DNA" herein is used generally and refers to both DNA and RNA. The addition of a pair of swarm primers may improve upon LAMP reactions for a variety of reasons, such as an increased ability to take advantage of nicks in double-stranded DNA, increased production of amplicons resulting in greater rates of early-stage amplicons, and/or providing strand displacement. The swarm primers provide for strand displacement downstream from the LAMP reaction site, annealing to the opposite DNA strand from the LAMP reaction site and opens up the DNA or RNA in the opposite direction of the LAMP reaction site, thus staying clear of the LAMP reaction. Furthermore, the swarm primers provide strand displacement of double-stranded DNA without the use of heat or chemical denaturation.

An embodiment of the invention provides an improved LAMP reaction by utilizing a pair of swarm primers, an inner primer and an outer primer, with or without the use of F3/B3 displacement primers.

Another embodiment of the invention provides an improved LAMP reaction by utilizing a pair of swarm primers, an inner primer and an outer primer along with one or more of: F3/B3 displacement primers, loop primers, and stem primers.

An embodiment of the invention is directed to increasing the reaction speed of LAMP reactions.

Yet other embodiments of the invention are directed to reducing variability, increasing sensitivity, increasing signal production, reducing energy cost and equipment complexity and lowering the limits of detection, thus reducing cost.

Still other objects and advantages of the invention will in part be obvious and will in part be apparent from the specification. Other features and advantages of this invention will become apparent in the following detailed description of exemplary embodiments of this invention with reference to the accompanying drawings.

BRIEF DESCRIPTION OF THE DRAWINGS

For a fuller understanding of the invention, reference is made to the following description taken in connection with the accompanying drawing, in which:

FIG. 3F is an illustration of a part of the reaction principle of the embodiment of FIG. 3A;

FIG. 3G is an illustration of a part of the reaction principle of the embodiment of FIG. 3A;

FIG. 4A is an illustration of parts of the reaction principle of the embodiment of FIG. 3A;

FIG. 4B is an illustration of parts of the reaction principle of the embodiment of FIG. 3A;

FIG. 4C is an illustration of parts of the reaction principle of the embodiment of FIG. 3A;

FIG. 7F is an illustration of parts of the reaction principle of the embodiment of FIG. 7A;

FIG. 10 is an illustration of an example of the increasing effect of swarm primers on reaction speed.

FIG. 11 is an illustration of an example of the effect of the concentration of FIP/BIP or F3/B3 on reaction speed.

FIG. 12 is an illustration of an example of the analytical performance increases associated with using swarm primers, as tracked using the intercalating dye EvaG;

FIG. 13A is an illustration of the increased signal production as a result of the addition of swarm primers to the HNB reaction;

FIG. 13B is an illustration of an example of reduced variability associated with swarm primers;

FIG. 18 shows the positions of sequences of primers used for the amplification of a gene;

FIG. 20 shows the result of LAMP reactions with or without F1S/B1S swarm primers; and FIG. 21 illustrates graphs indicating examples of the superpositioning of LAMP amplicon products when two sets of primers are used.

DETAILED DESCRIPTION OF THE PREFERRED EMBODIMENTS

The invention generally is directed to nucleic acid amplification technology, more particularly to isothermal amplification techniques such as loop-mediated isothermal amplification (LAMP). As discussed above, whereas PCR is an effective means of amplification, because of the high cost of equipment, sensitivity to contamination, and other drawbacks, isothermal methods such as LAMP may be preferred in certain situations. For example, when amplification is being performed outside of a laboratory where equipment is limited and quick results are needed, or in underdeveloped regions where they cannot afford expensive equipment, the LAMP method may be preferred.

Unlike PCR, LAMP does not require thermal cycling. Whereas the initial DNA denaturation step in LAMP requires the use of heat (or a chemical), the remainder of the reactions do not. More specifically, a double-stranded DNA undergoes denaturation, thus separating the double-stranded DNA into two single-strands and exposing the reaction sites along each DNA strand, after which the LAMP occurs using inner primers FIP, BIP and outer primers F3, B3.

Swarm Primers F1S, B1S

The addition of swarm primers described herein may significantly increase the rate of amplification regardless of whether or not the target nucleic acid is heat denatured. In accordance with one embodiment, it may be beneficial to introduce swarm primers in lieu of performing heat or chemical denaturation, especially when a particular template is sensitive to heat or chemical methods, such as Lambda phage DNA which degrades within minutes upon exposure to 95 degree Celsius treatments. Thus, results of diagnostic tests may be obtained more expeditiously than previously available methods, such as LAMP. Moreover, because amplification occurs at a higher speed, the risk of false positives occurring may be decreased, thus increasing the specificity of a test. Additionally, the addition of swarm primers increases signal production for certain tests, which may be attributable to a volume of swarm amplicons that are formed as a by-product of the reactions. Furthermore, the addition of swarm primers may increase the rate of amplification even if one or more primers, such as the outer primers F3, B3, loop primers FL, BL or stem primers Fstem, Bstem are omitted. Thus, the process may differ from the traditional LAMP method while providing a new method comprising inner primers and swarm primers.

Figure 2:
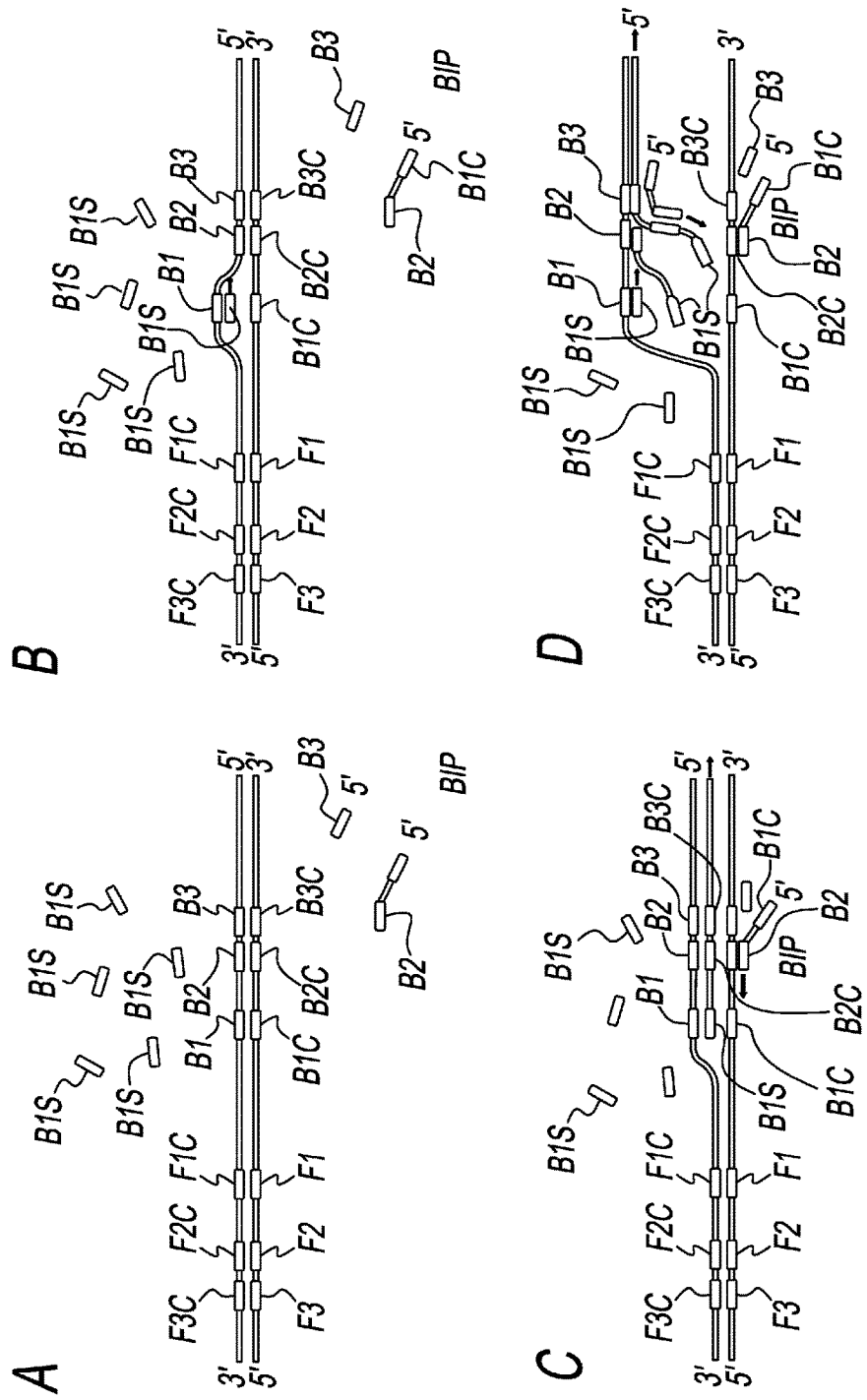
FIG. 2 is an illustration of swarm initiation.

As mentioned briefly above, swarm primers F1S, B1S may be introduced to a double-stranded DNA sample to initiate the LAMP reaction, more specifically they may separate portions of a double-stranded DNA to provide segments of single-stranded DNA, onto which an inner primer FIP, BIP may bind, as illustrated in FIG. 2. The conventional LAMP requires the sample DNA to undergo extreme temperature exposure, for example, 95° C. for 5 minutes followed by immediate 0° C. holding. Alternatively, it must undergo extreme chemical treatments, which usually require subsequent wash stages to avoid interference with the amplification reactions. These methods of denaturation are undesirable in resource-limited settings, for example, when used with portable or disposable instruments.

Figure 3A:
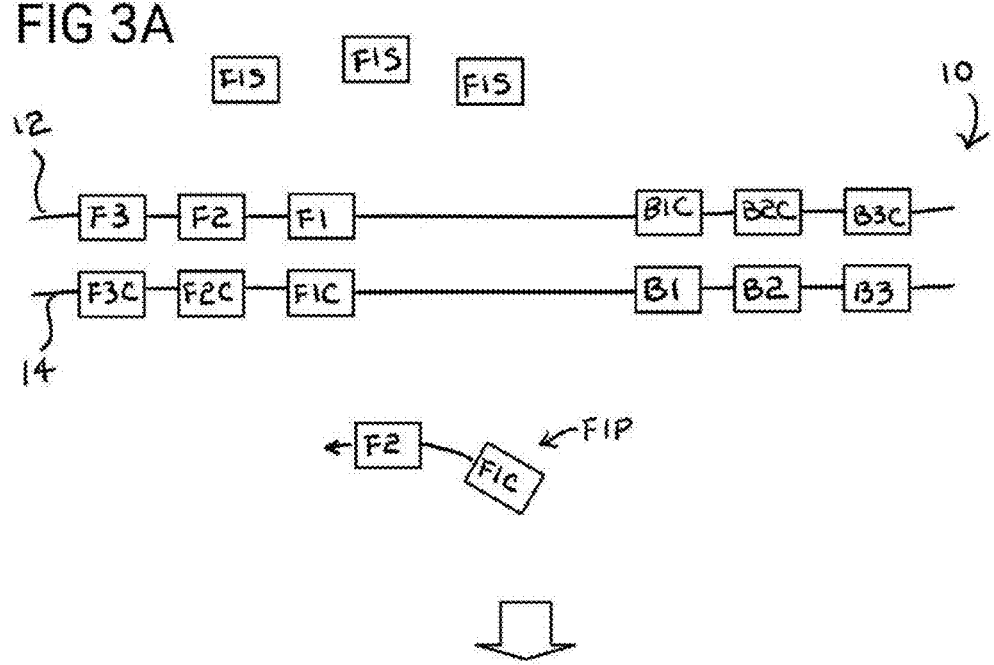
FIG. 3A is an illustration of a part of the reaction principle in accordance with an embodiment of the invention.
Figure 3B:
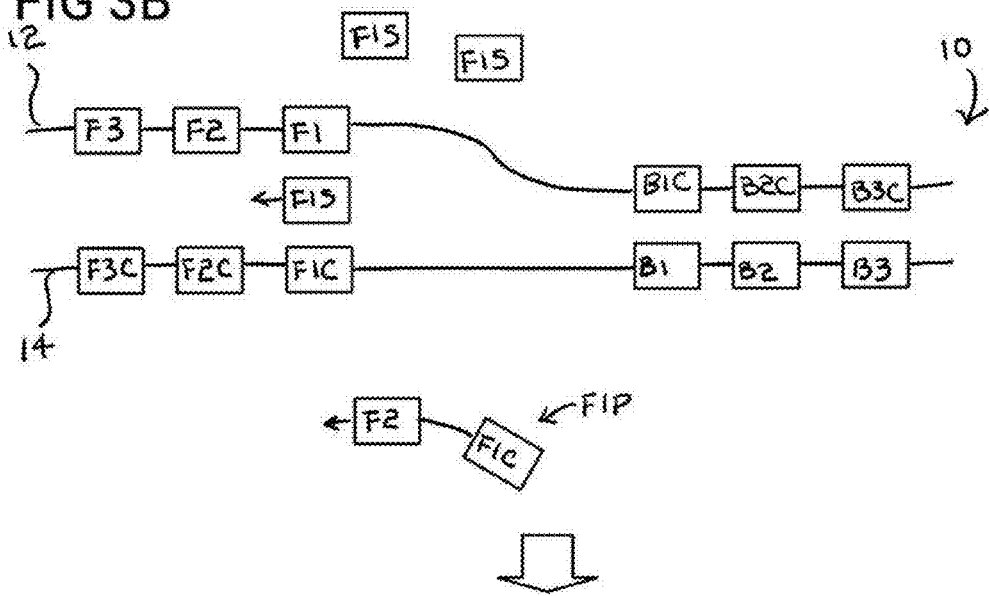
FIG. 3B is an illustration of a part of the reaction principle in accordance with an embodiment of the invention.
Figure 3C:
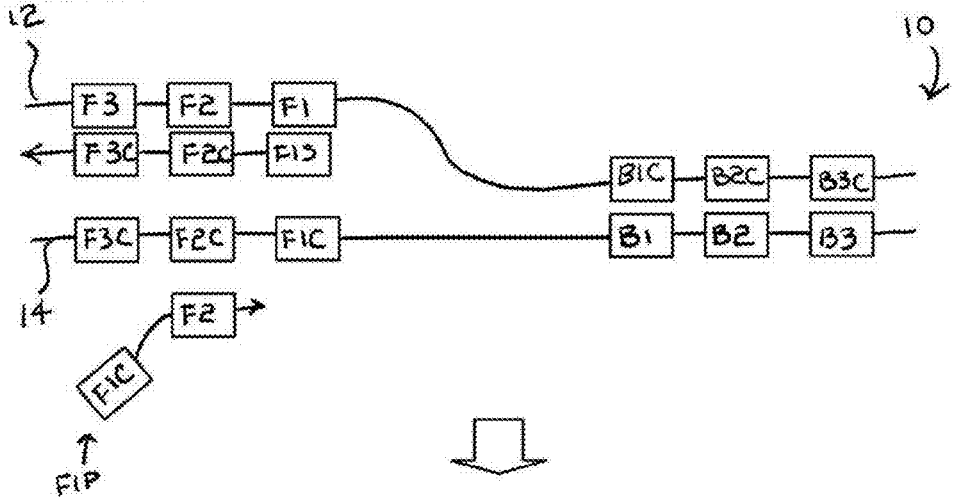
FIG. 3C is an illustration of a part of the reaction principle of the embodiment of FIG. 3A.
Figure 3D:
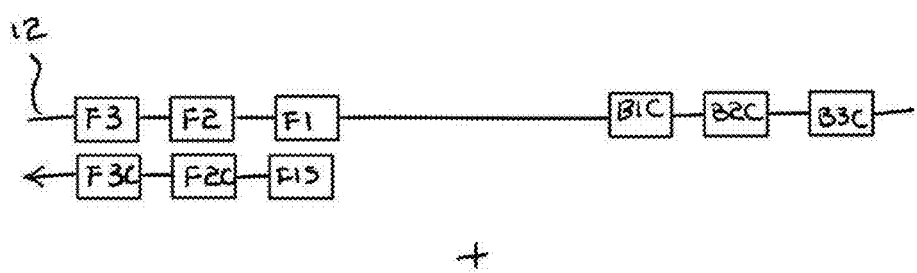
FIG. 3D is an illustration of a part of the reaction principle of the embodiment of FIG. 3A.

Reference is made to FIGS. 3A-3D. FIG. 3A illustrates a double-stranded DNA 10 with the addition of primers FIP and F1S. FIG. 3B illustrates a swarm primer F1S binding to a double-stranded DNA 10. As shown, a swarm primer F1S anneals to the F1 region of first strand 12 of the double-stranded DNA 10, thus separating strands 12 and 14 proximate the F1 site. The F1 site is downstream of the FIP primer target F2, on the opposite strand. Whereas the FIP primer anneals to strand 14, swarm primer F1S anneals to strand 12. Preferably, swarm primer F1S substantially overlaps the F1 region and initiates polymerase extension toward F2, thus opening up the double-stranded DNA 10, separating strands 12, 14 and exposing F2C and F3C, the recognition sites for inner primer FIP and outer primer F3, respectively.

Figure 3E:
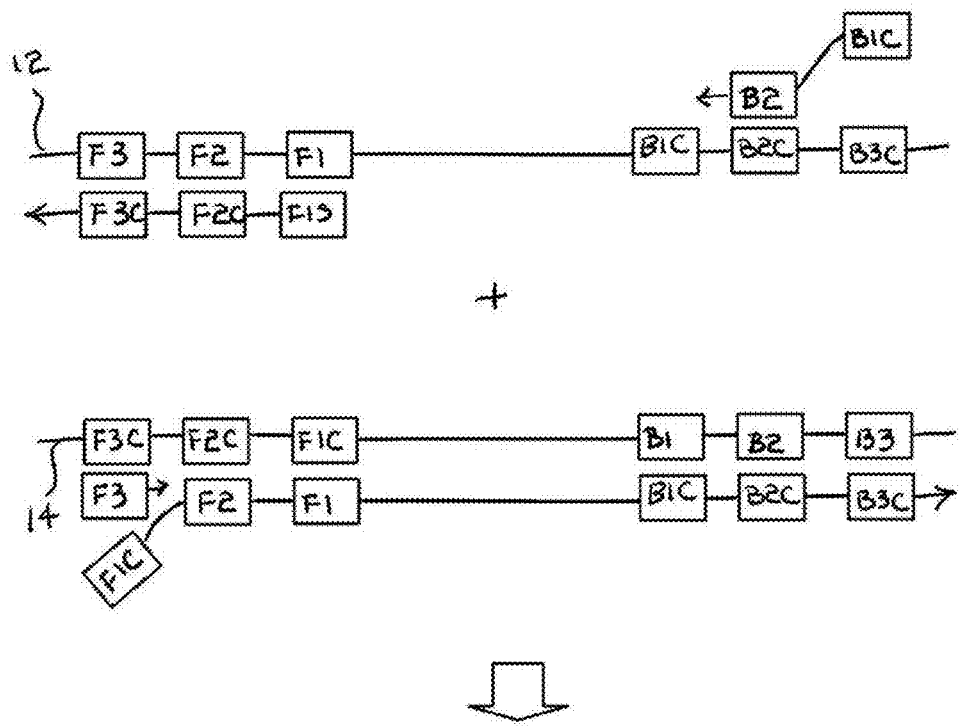
FIG. 3E is an illustration of a part of the reaction principle of the embodiment of FIG. 3A.

In the embodiment illustrated, FIP primer then anneals to F2C and initiates synthesis of a complementary chain 16 in the direction of F1C, displacing the remainder of strand 14 from strand 12. As illustrated in FIG. 3E, an outer primer F3 anneals to the F3C region of strand 14, and initiates strand displacement DNA synthesis in the direction of F1C, thus displacing chain 16 formed from the FIP primer and forming a double-stranded amplicon 30, which is a copy of the original target DNA; see FIG. 3F. Generally in LAMP, the double-stranded DNA comprising strand 14 and the strand formed from outer primer F3 are not involved in the subsequent steps of LAMP because it would require thermal or chemical denaturation to separate the DNA strands again for the inner primers' recognition sites to become exposed. However, in accordance with an embodiment of this invention, the cycle described above repeats itself with each newly formed double-stranded amplicon 30. Because the swarm primers F1S, B1S can anneal to the double-stranded amplicon 30 to expose the inner primers' recognition sites without the use of heat or chemicals, the cycle above illustrated in FIGS. 3A to 3F may be repeated on the each double-stranded amplicon 30 formed.

Figure 1:
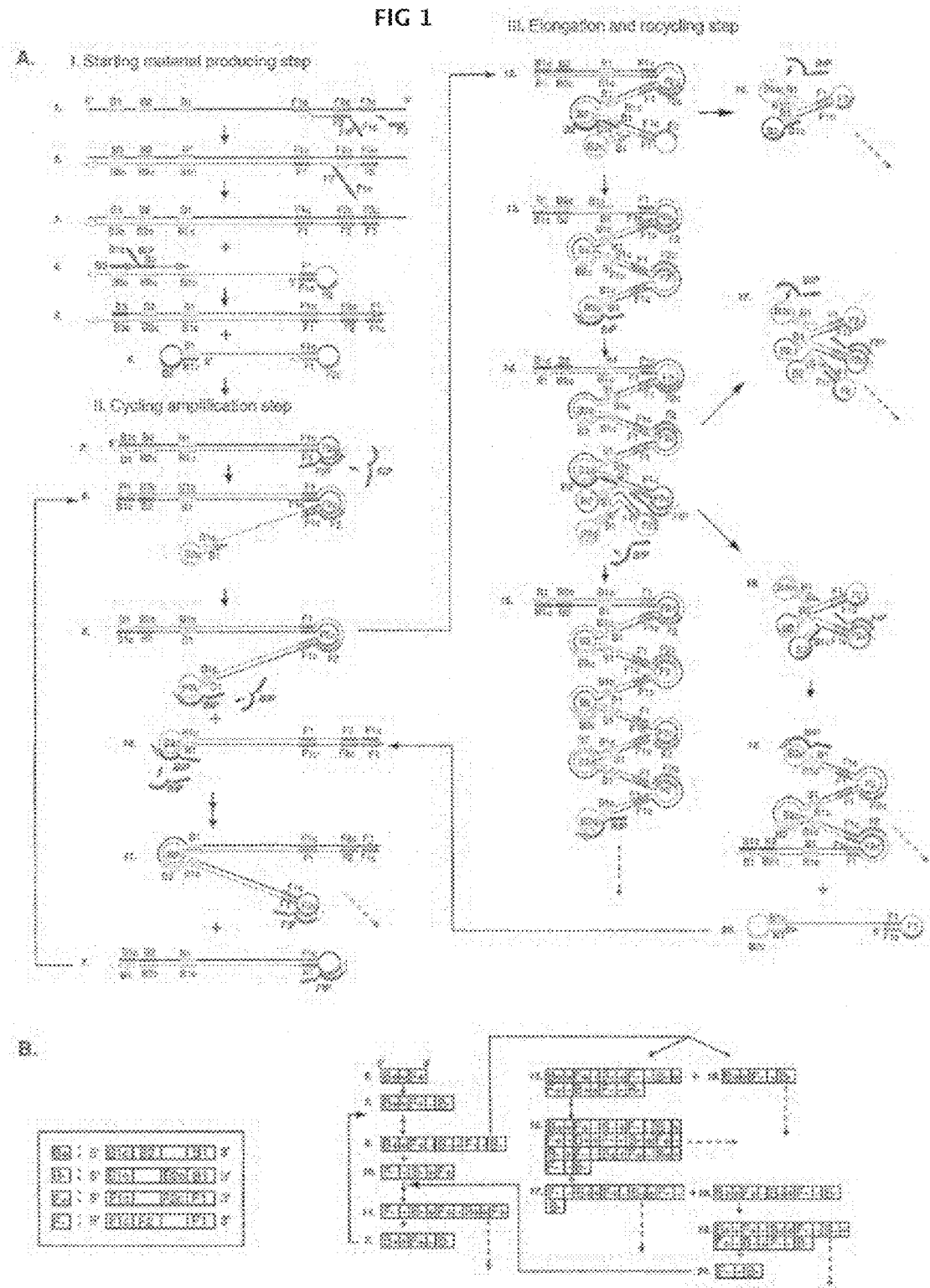
FIG. 1 is an illustration of Loop-mediated isothermal amplification of DNA.

As shown in FIG. 3F, strand 16 self-anneals to form a loop at the 5' side, wherein F1 and F1C anneal to each other to form a loop containing F2, thus forming a first single-loop amplicon 20, which corresponds to structure 4 of FIG. 1, and may follow the LAMP process illustrated therein. More specifically, inner primer BIP anneals to B2C of strand 16 and initiates strand displacement DNA synthesis in the direction of B1C, which is then displaced by strand displacement DNA synthesis initiated upon outer primer B3 annealing to the B3C site toward B2C. Thus, as illustrated in FIG. 3G, a dumbbell amplicon 40 having two loops is formed, having one loop at the 5' side where B1C anneals to B1 to form a first loop 42 containing B2, and another loop at the 3' side where F1 anneals to F1C to form a second loop 44 containing F2C. The dumbbell amplicon 40 corresponds to structure 6 in FIG. 1, and converts to a stem-loop amplicon by self-primed DNA synthesis (structure 7), the starting material for LAMP cycling as described above.

Likewise, strand 12, which was displaced from strand 14, is displaced from the swarm primer amplicon upon backward inner primer BIP's strand displacement DNA synthesis. The strand synthesized by the BIP primer is then displaced by outer primer B3, resulting in a second single-loop amplicon 25 and a double-stranded amplicon 30, which as described above is a reproduction of the original target DNA strand 10. The cycle may thus be repeated for double-stranded DNA 30.

As shown in FIG. 3G, along with dumbbell amplicon 40, a second double-stranded amplicon 50 comprising strand 16 is also formed, which corresponds to structure 5 in FIG. 1. Similar to the double-stranded DNA 30 previously mentioned, this second double-stranded amplicon 50 is not involved in the LAMP process shown in FIG. 1. However, with the use of swarm primers F1S, B1S in accordance with an embodiment of the invention, the second double-stranded amplicon 50 may also be split and amplified, thus increasing the pool of the target DNA sequence available for amplification once again.

FIGS. 4A to 4E illustrate an exemplary chain of reactions that the second double-stranded amplicon 50 may undergo. As swarm primer F1S splits the strands near F1 region, F1 of the displaced strand self-anneals with F1C to form a loop containing F2C and initiate self-primed strand displacement DNA synthesis to create a third single-loop amplicon 60. Also resulting from the reaction is a partially double-stranded amplicon which, upon backward inner primer BIP and outer primer B3 annealing thereto, results in a second double-stranded amplicon 50 and a dumbbell amplicon 40 for LAMP cycling, along with a swarm amplicon 93, which is discussed below.

Figure 4D:
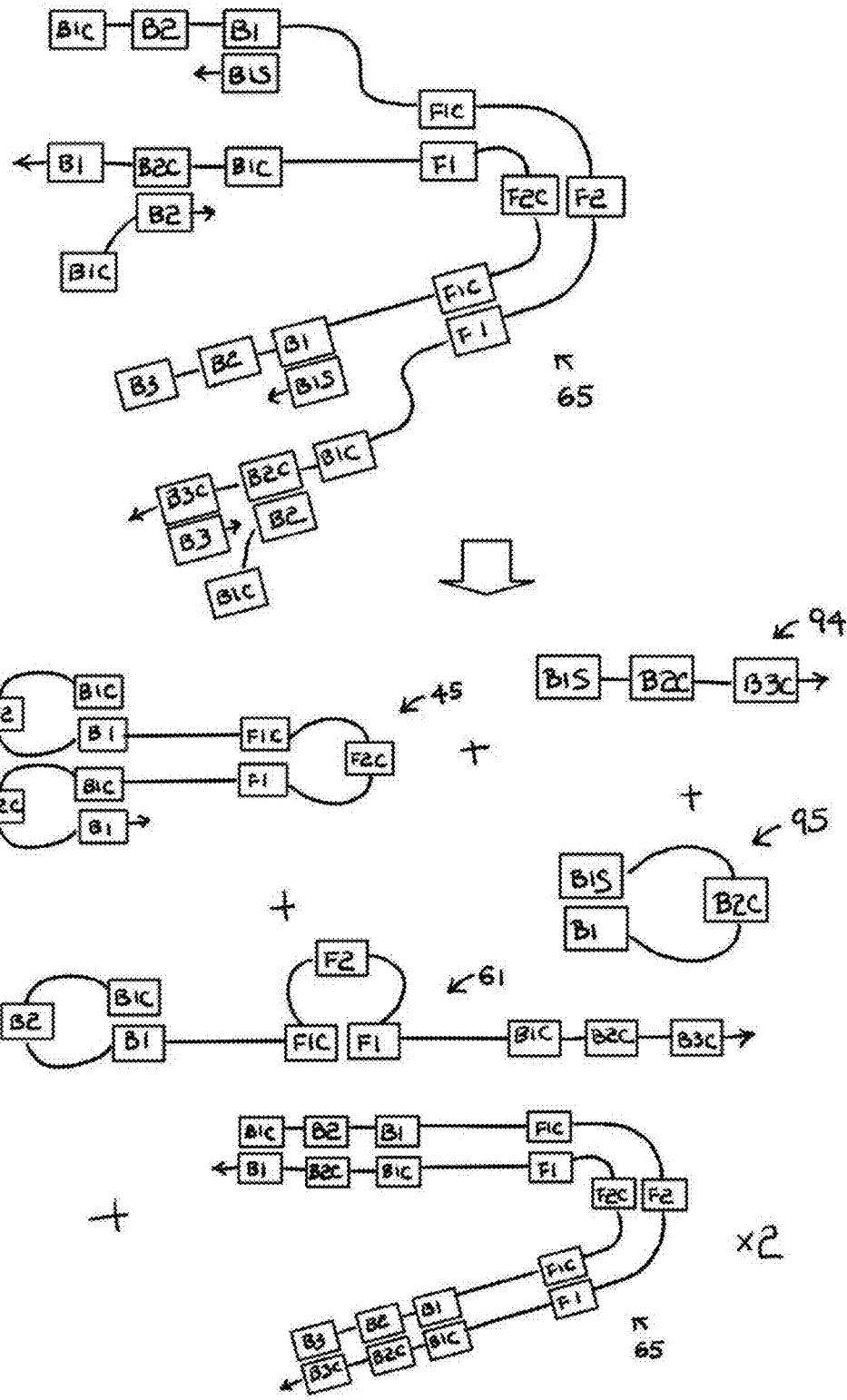
FIG. 4D is an illustration of parts of the reaction principle of the embodiment of FIG. 3A.

Referring to FIG. 4B, a swarm primer B1S may anneal to B1 region, thus splitting up the strands to free B2C region for backward inner primer BIP to anneal thereto. Also as shown, forward inner primer FIP may anneal to F2C region of the single-strand loop. The resulting amplicons include first single-loop amplicon 20, which as described above, results in a dumbbell amplicon 40 for LAMP cycling. Also formed are a swarm amplicon 94, a first extended single-strand amplicon 61, and a first extended double-stranded amplicon 62. Referring to FIG. 4C, the reaction of backward inner primer BIP and backward outer primer B3 with the first extended single-strand amplicon 61 results in a triple-loop amplicon 45, which corresponds to structure 16 of FIG. 1, which is further into the LAMP cycle than dumbbell amplicon 40. Also created is a second extended double-stranded amplicon 65. In FIG. 4D, one example of second extended double-stranded amplicon 65 annealing to a plurality of swarm primers is shown, and some of the reactions that follow. As shown, when swarm primer B1S anneals to B1 region and displaces the strands from each other proximate B1 region, B2 regions are exposed, and thus have backward inner primers BIP anneal thereto, followed by backward outer primer B3 annealing to B3 region when available. The resulting amplicons include swarm amplicons 94, 95, triple-loop amplicon 45, first extended single-strand amplicon 61 and two copies of second extended double-stranded amplicon 65. Therefore, this cycle illustrated in FIGS. 4C to 4D may repeat to create more triple-loop amplicons 45 for LAMP cycling.

Figure 4E:
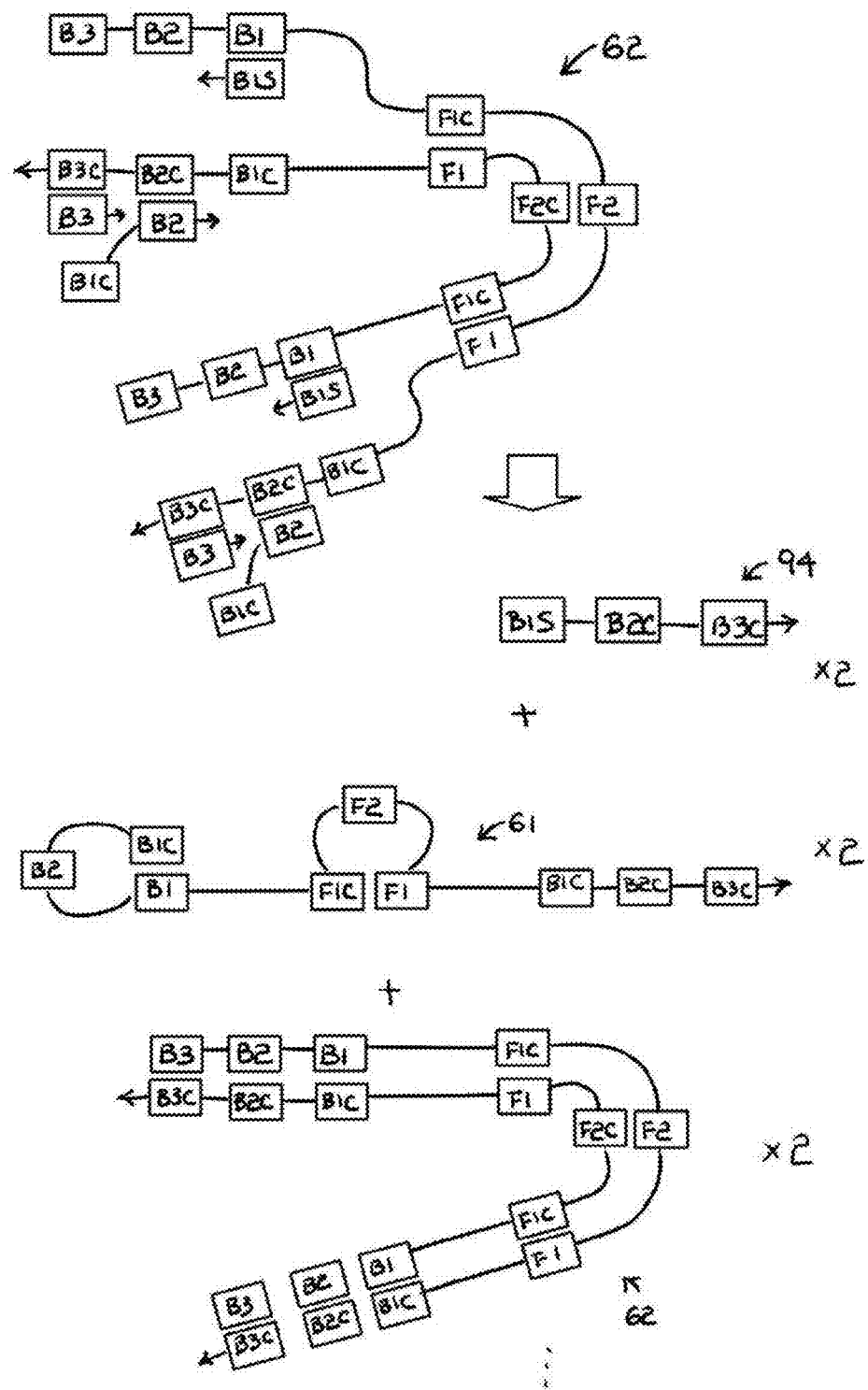
FIG. 4E is an illustration of parts of the reaction principle of the embodiment of FIG. 3A.

Reference is made to FIG. 4E, wherein first extended double-stranded amplicon 62 is split by swarm primers B1S, then annealed to by backward inner primer BIP and backward outer primer B3. The resulting amplicons are two copies of swarm primers 94, two copies of first extended single-strand amplicon 61 and two copies of first extended double-stranded amplicon 62, thus repeating the cycle shown in FIGS. 4C to 4D to create triple-loop amplicons 45 for LAMP cycling.

Figure 5:
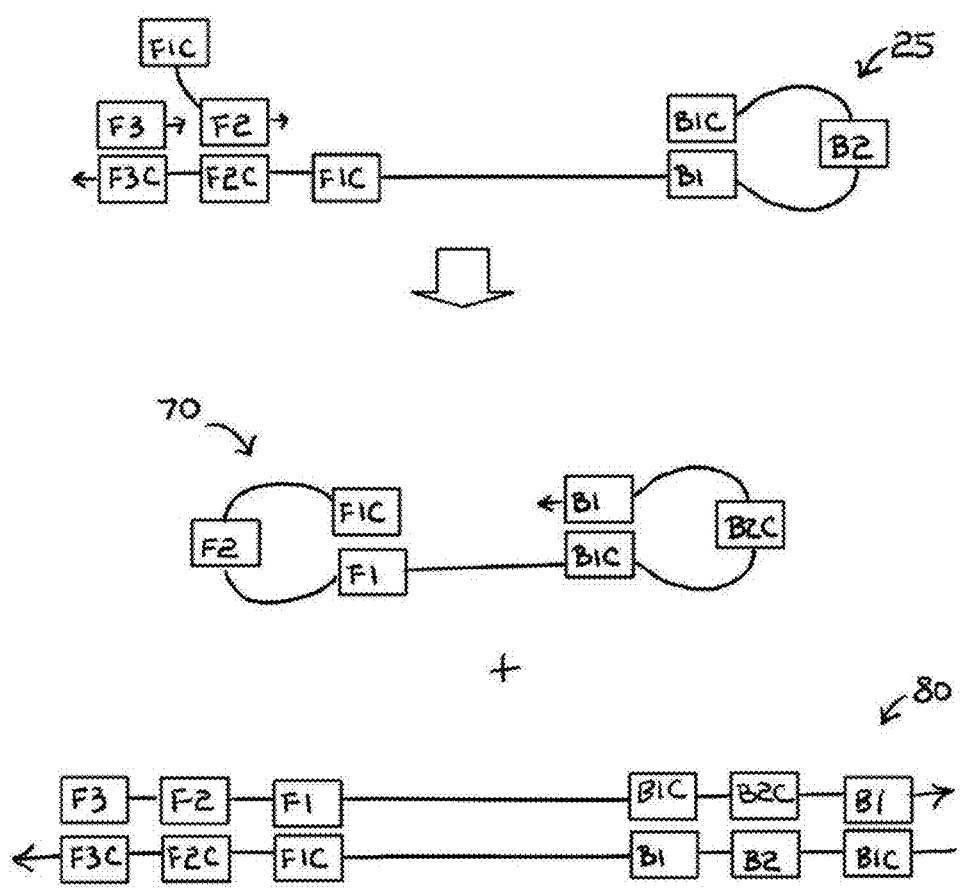
FIG. 5 is an illustration of a reaction principle of an amplicon of FIG. 3G.

Second single-loop amplicon 25 shown in FIG. 3G includes a single-strand portion, and is thus exposed for forward inner primer FIP to anneal thereto, which may be displaced by an outer primer F3 as illustrated in FIG. 5. Thus, a dumbbell amplicon 70 for LAMP cycling, along with and a third double-stranded amplicon 80 are formed. Once again, this newly formed double-stranded amplicon 80 may also be split by swarm primers F1S, B1S to begin yet another chain of reactions resulting in more dumbbell amplicons 40, 70 for LAMP cycling as well as other amplicons not described in detail.

Hence, whereas under traditional LAMP, a single target DNA strand would typically produce two dumbbell amplicons 40, one for each strand, once swarm primers F1S, B1S are introduced, a single target DNA strand may result in the continuous formation of amplicons suitable for LAMP cycling, such as dumbbell amplicons 40 and triple-loop amplicons 45. Therefore, the addition of swarm primers may increase the rate of amplification exponentially.

Figure 6A:
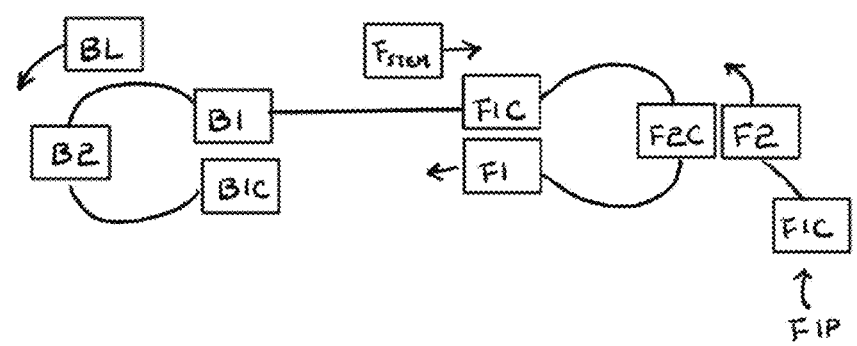
FIG. 6A is an illustration of a reaction principle of a dumbbell amplicon.
Figure 6B:
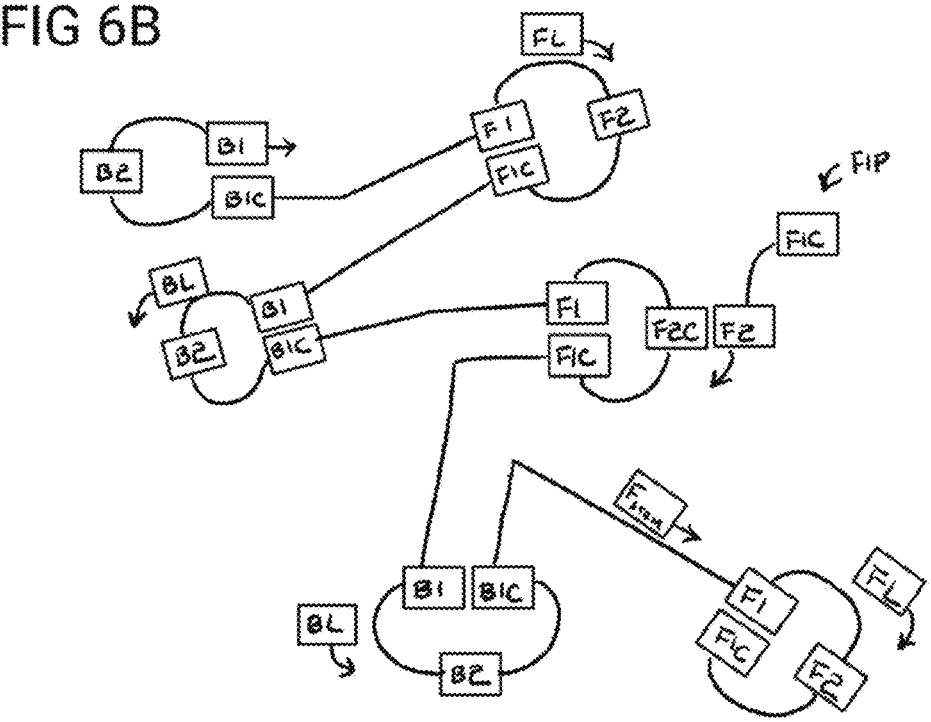
FIG. 6B is an illustration of a reaction principle of a dumbbell amplicon.

The rate of amplification may be further increased by the addition of loop primers FL, BL and/or stem primers Fstem, Bstem. FIGS. 6A and 6B illustrate a dumbbell amplicon 40 and an amplicon further along the LAMP process, respectively, having loop primers FL, BL and a stem primer Fstem annealed thereto in addition to inner primers FIP, BIP consistent with LAMP. Additional examples of amplicons to which loop primers may anneal and increase the rate of amplification include first extended single-strand amplicon 61, which includes two loops, neither of which are suitable for inner primers FIP, BIP to anneal to. Likewise, using stem primers with first extended single-strand amplicon 61, which includes two single-strands of the stem, may also enhance amplification.

As shown, adding loop primers FL, BL and stem primers Fstem, Bstem may increase the rate of amplification by utilizing more sites for amplification. Improvements observed when Swarm primers are added to conventional reactions with Loop primers may be at least partially due to, by way of non-limiting example, increased ability to take advantage of nicks in double-stranded DNA, increased production of amplicons due to new products created by swarm amplicons resulting in greater rates of early stage amplicons and a perceived increase in the rate of reaction, Swarm primers annealing to the template to provide strand displacement, or a combination thereof.

Omission of Outer Primers

Figure 7A:
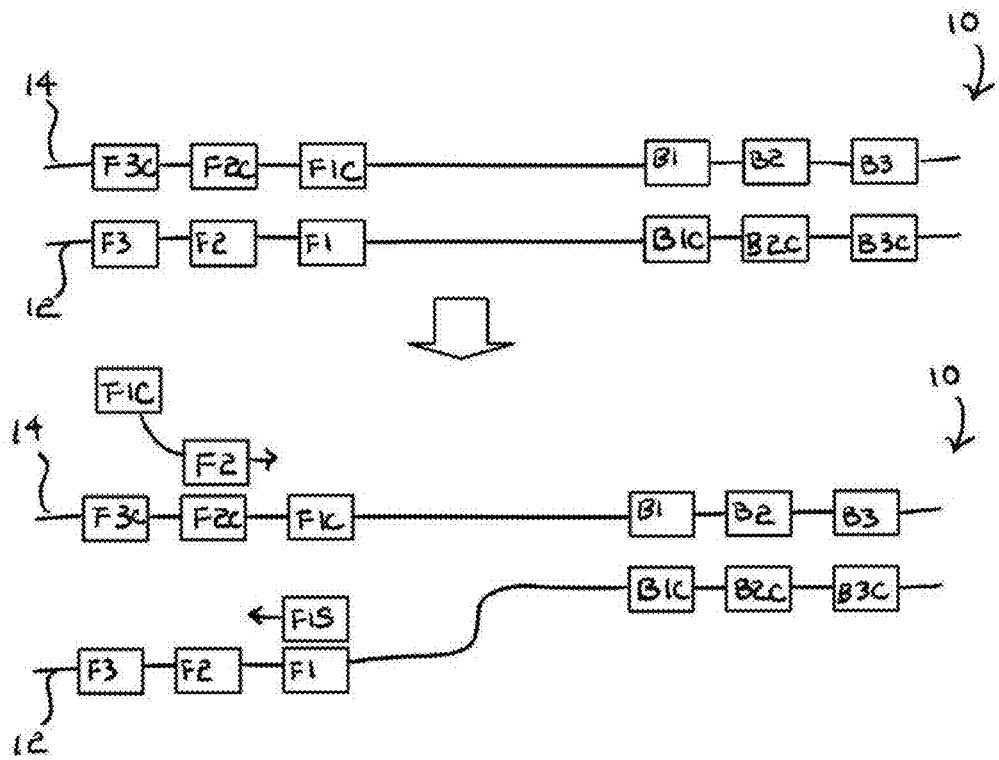
FIG. 7A is an illustration of parts of the reaction principle in accordance with another embodiment of the invention.
Figure 7B:
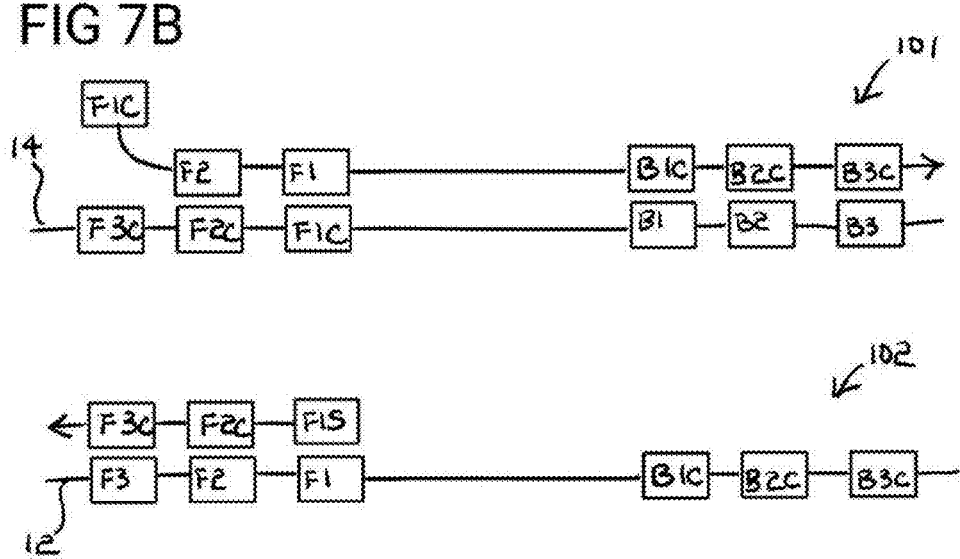
FIG. 7B is an illustration of parts of the reaction principle of the embodiment of FIG. 7A.
Figure 7C:
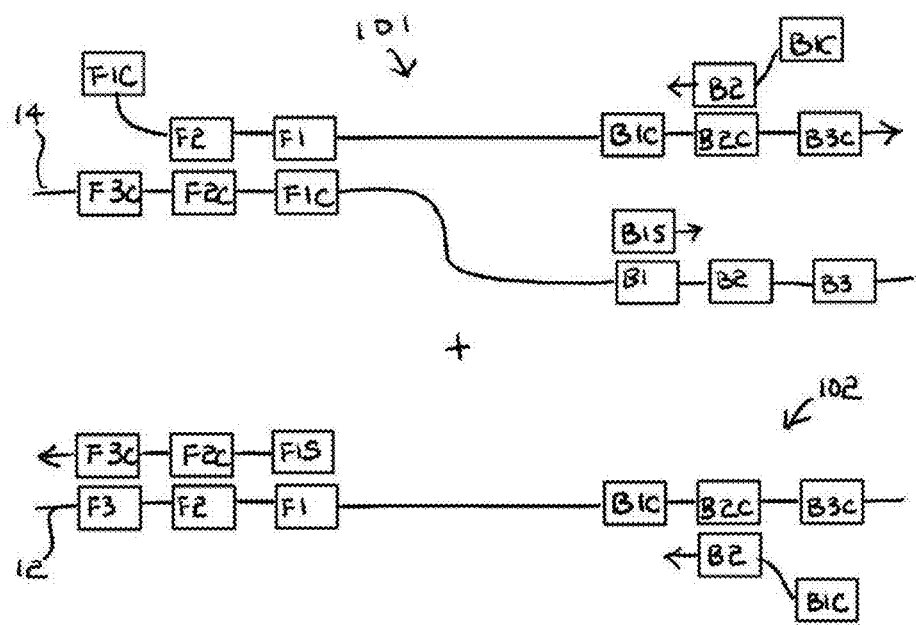
FIG. 7C is an illustration of parts of the reaction principle of the embodiment of FIG. 7A.
Figure 7D:
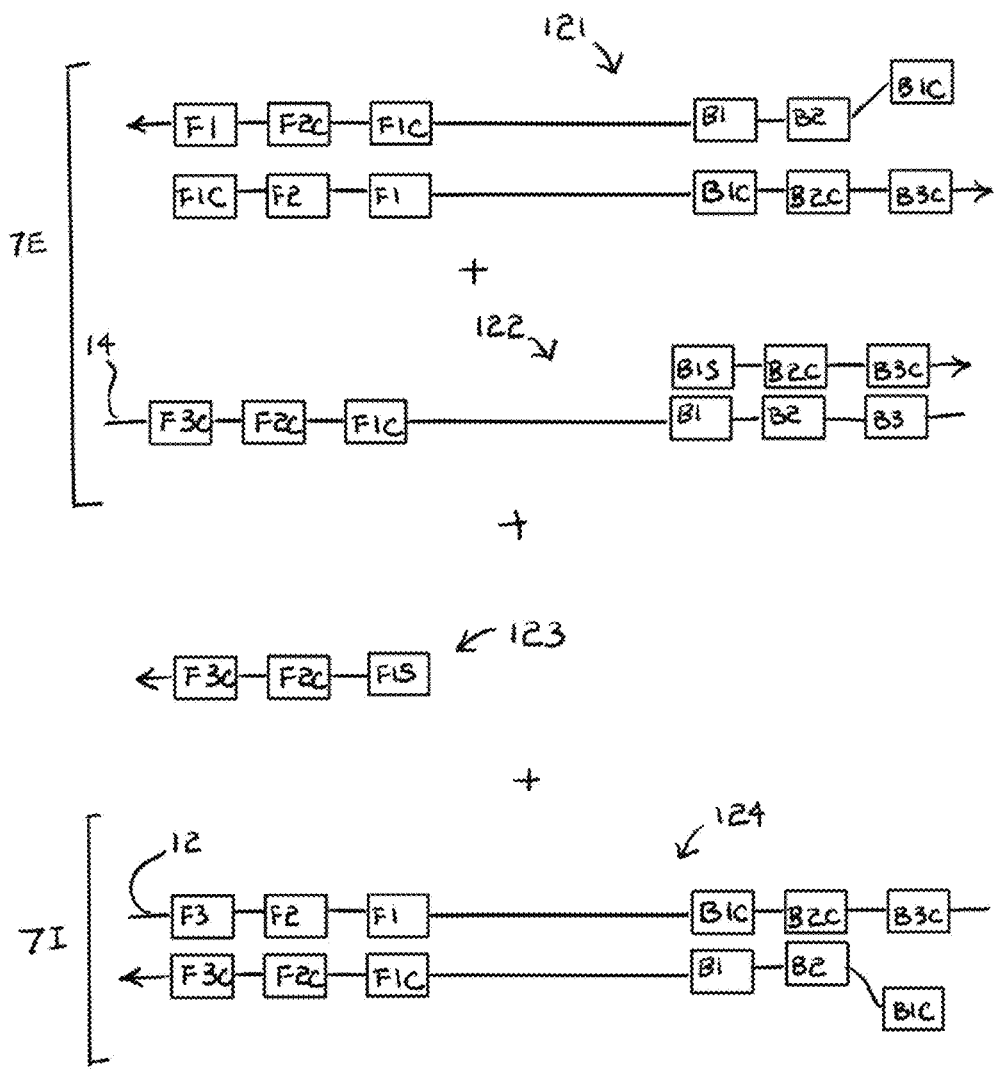
FIG. 7D is an illustration of parts of the reaction principle of the embodiment of FIG. 7A.
Figure 7E:
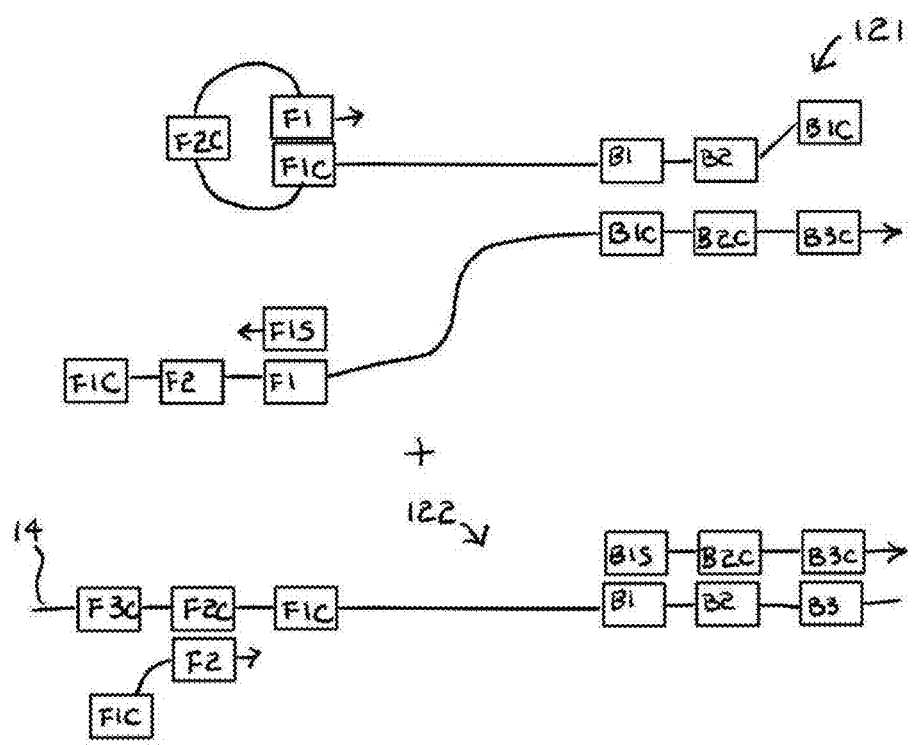
FIG. 7E is an illustration of parts of the reaction principle of the embodiment of FIG. 7A.
Figure 7G:
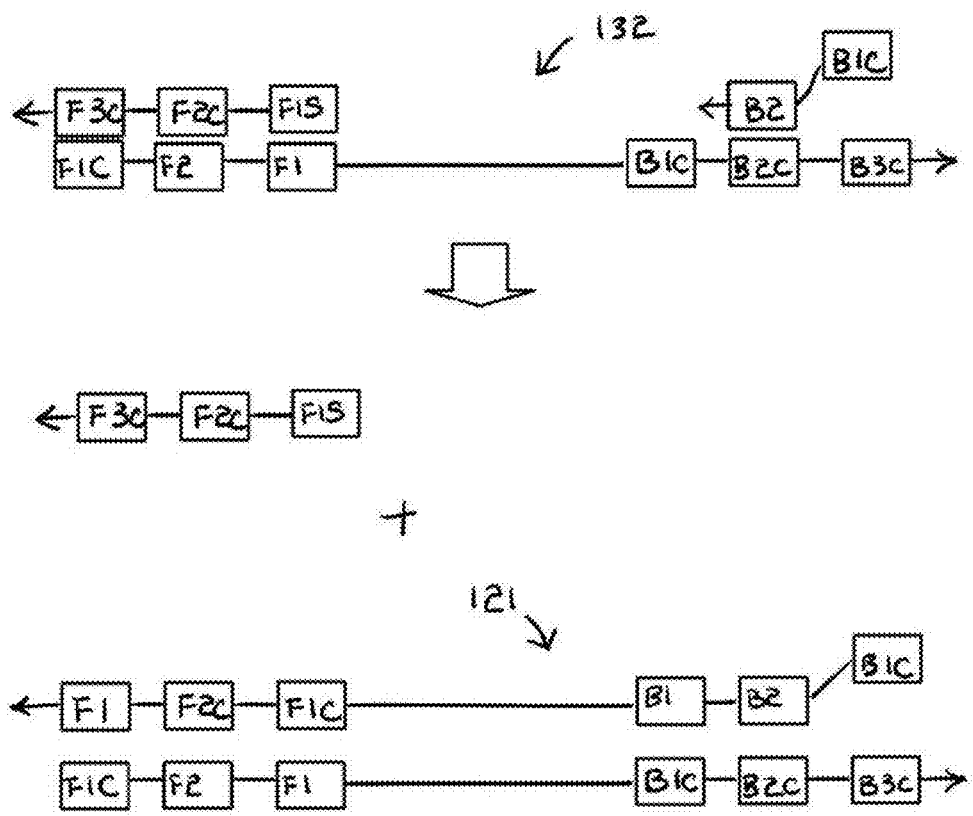
FIG. 7G is an illustration of parts of the reaction principle of the embodiment of FIG. 7A.
Figure 8A:
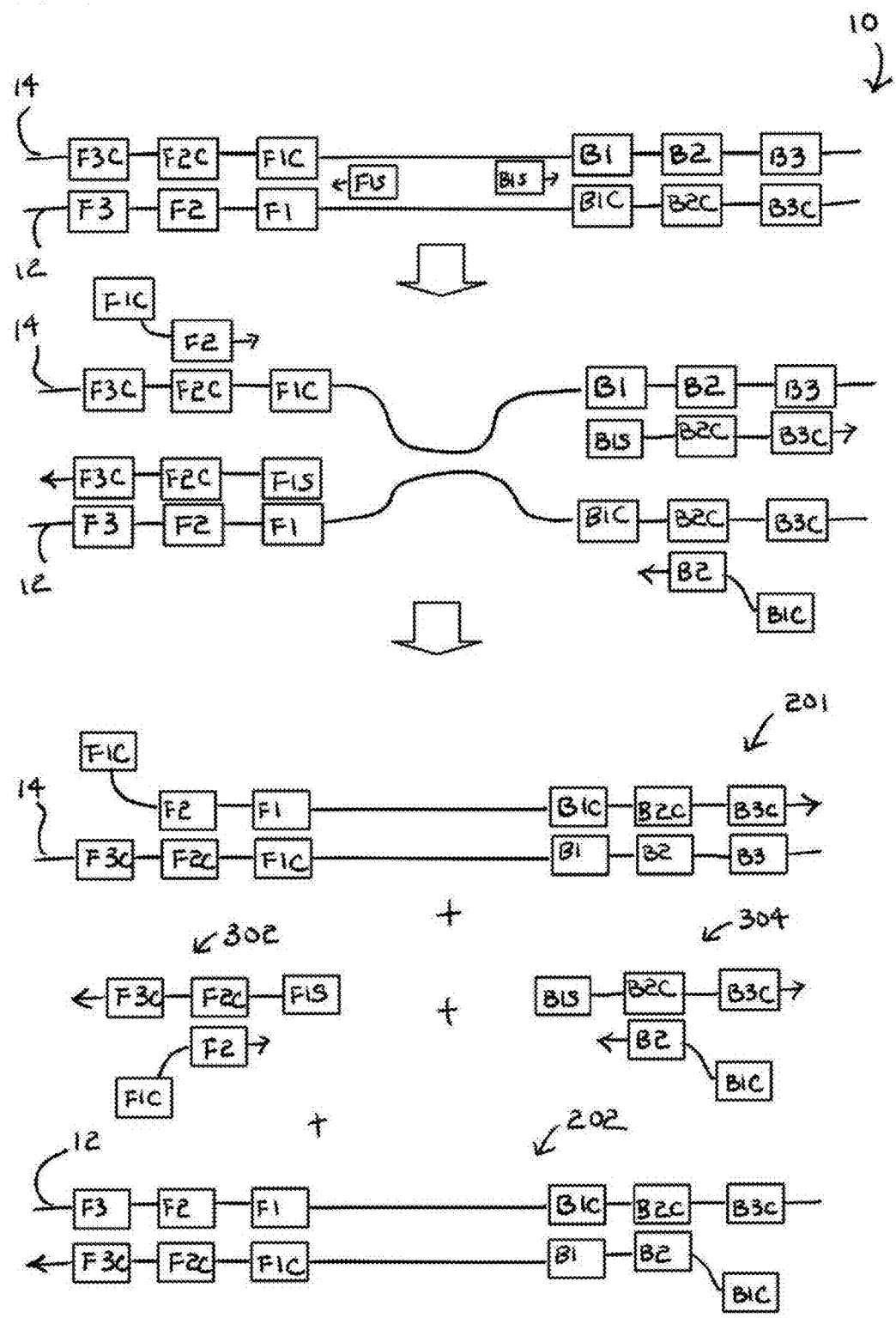
FIG. 8A is an illustration of parts of the reaction principle in accordance with another embodiment of the invention.
Figure 8B:
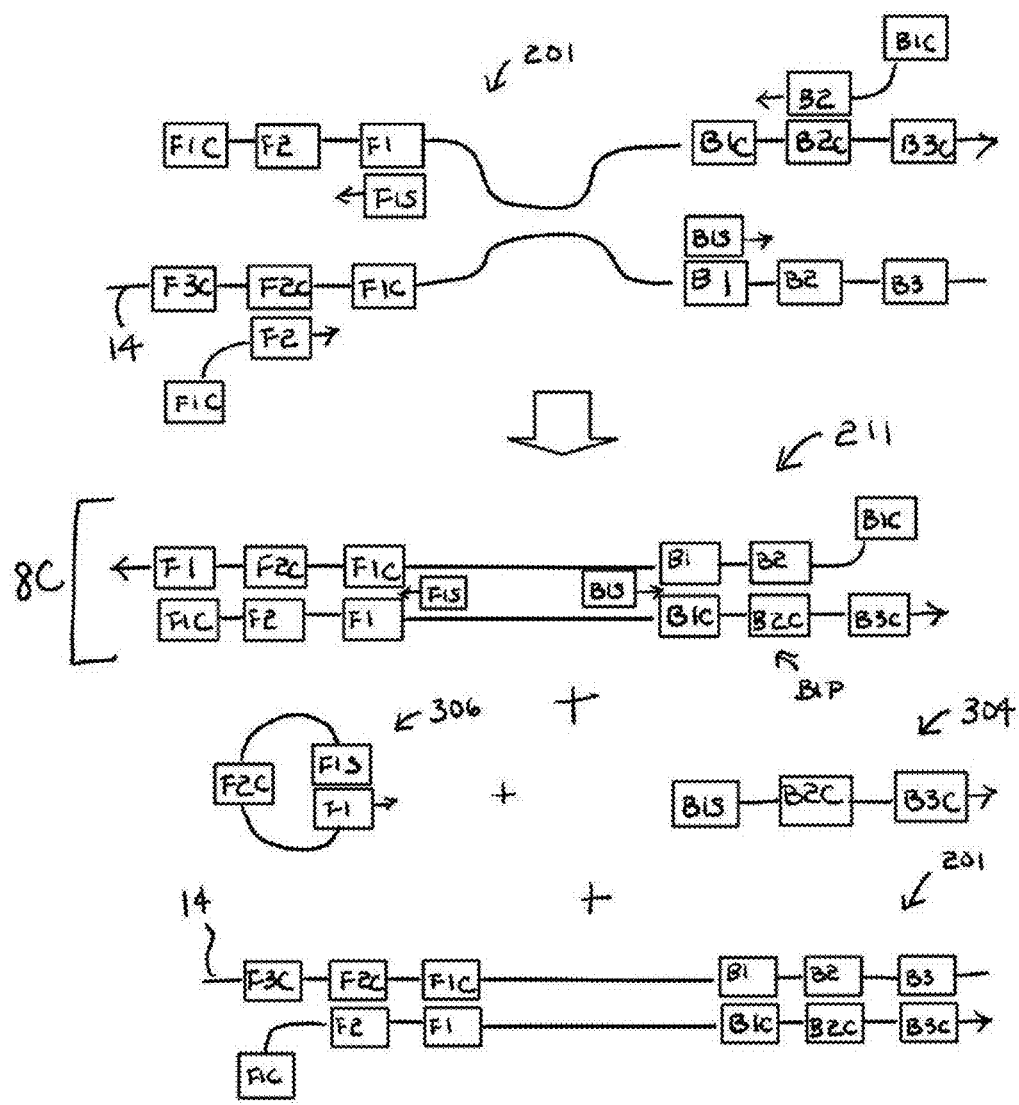
FIG. 8B is an illustration of parts of the reaction principle of the embodiment of FIG. 8A.
Figure 8C:
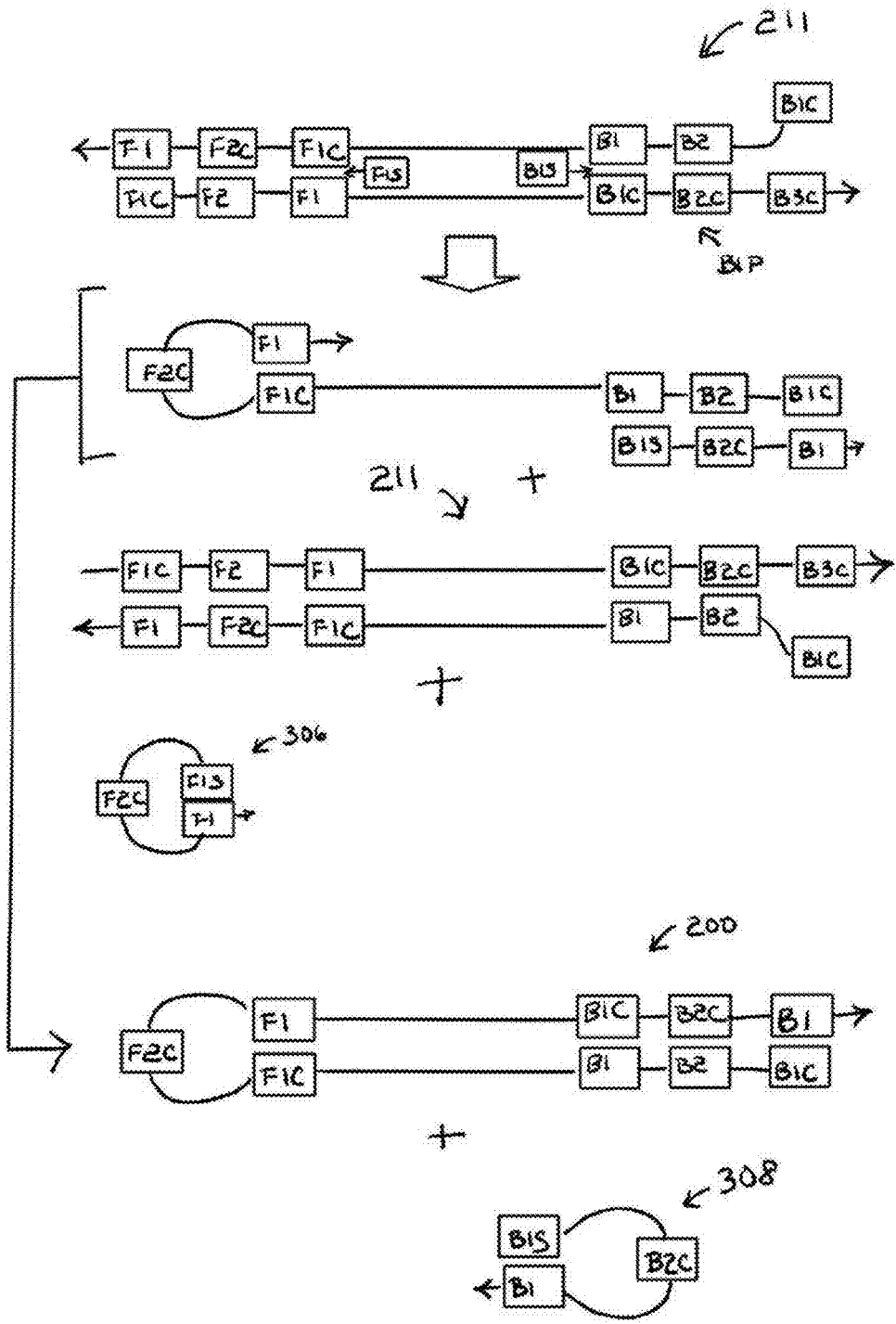
FIG. 8C is an illustration of parts of the reaction principle of the embodiment of FIG. 8A.
Figure 8D:
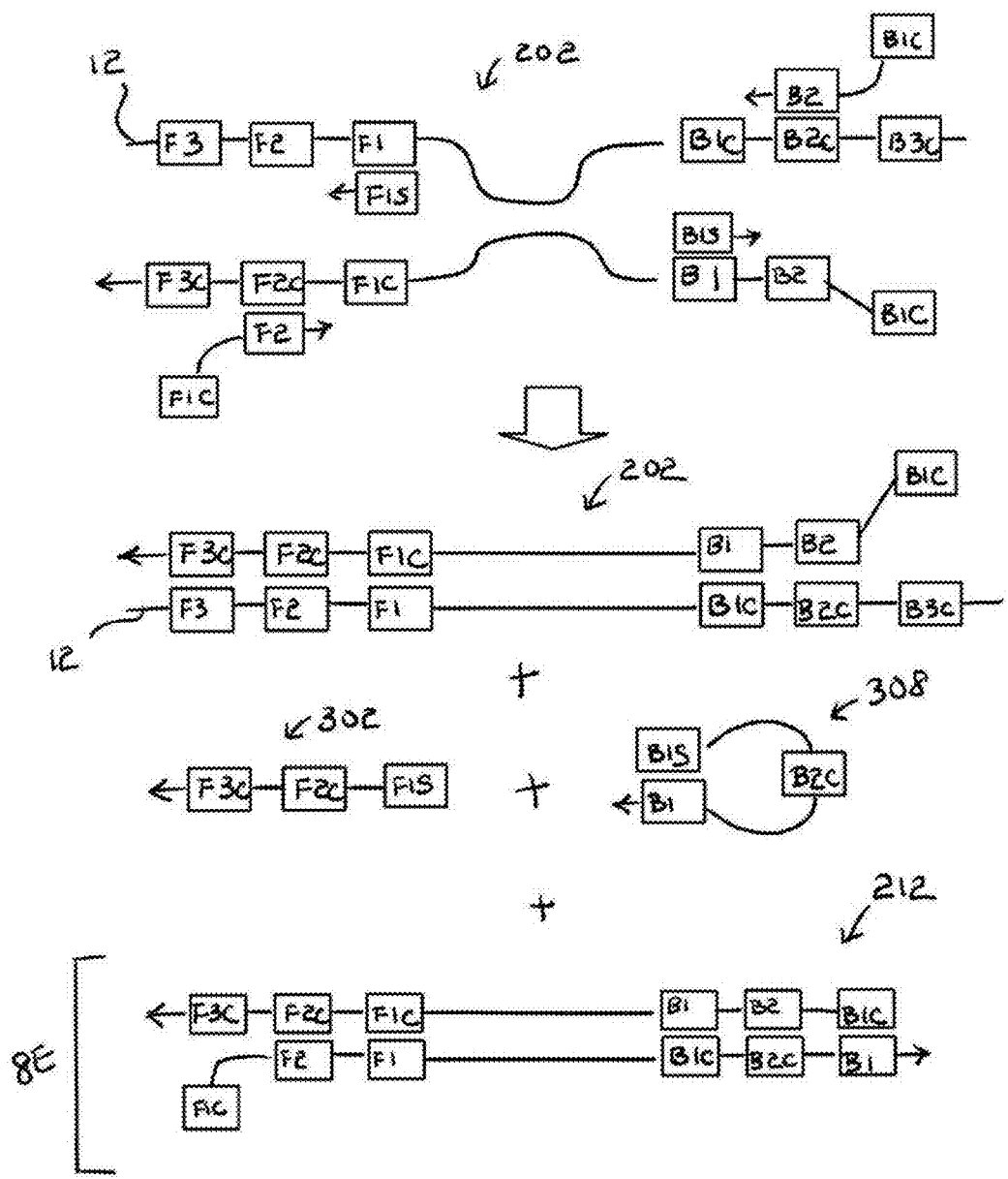
FIG. 8D is an illustration of parts of the reaction principle of the embodiment of FIG. 8A.
Figure 8E:
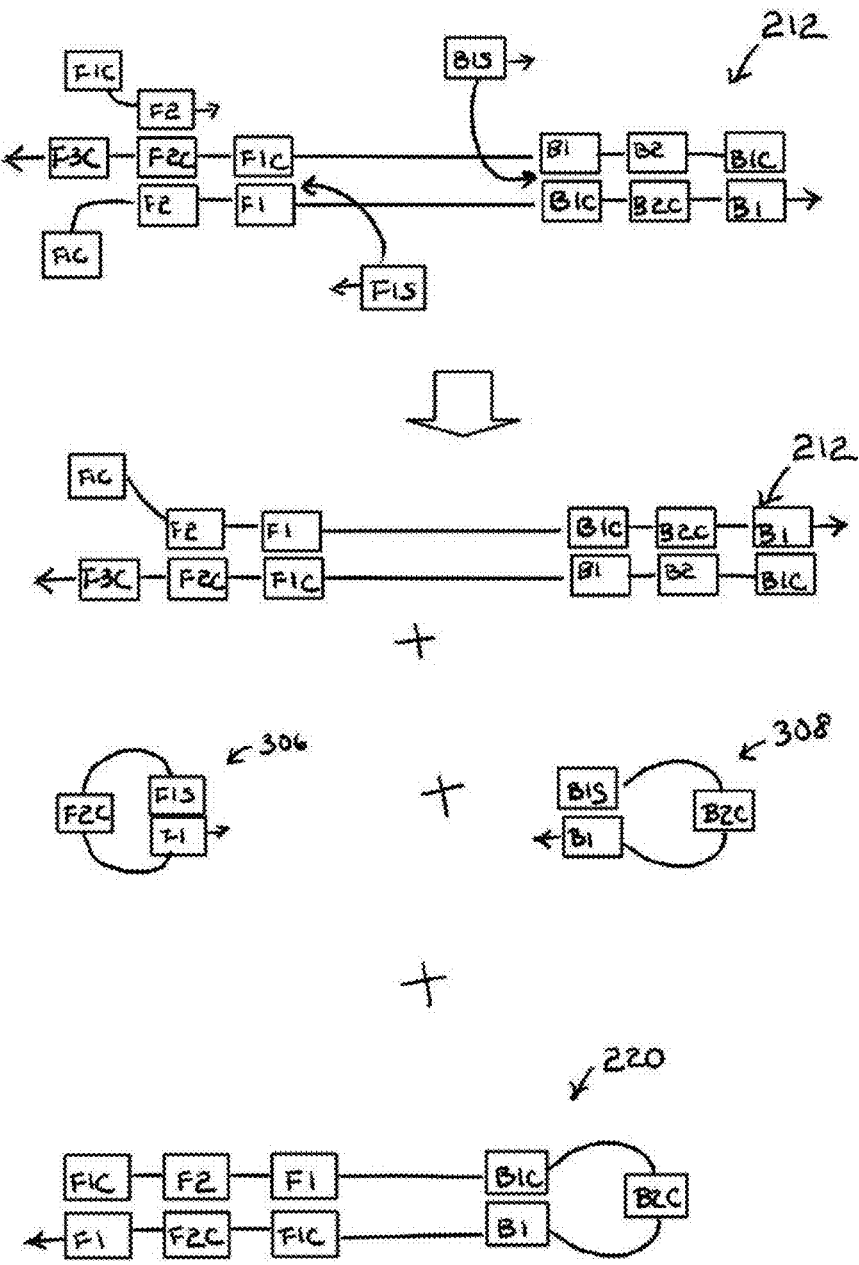
FIG. 8E is an illustration of parts of the reaction principle of the embodiment of FIG. 8A.

The employment of swarm primers may allow for the omission of the outer primers F3, B3 typically used in LAMP. For example, in accordance with certain embodiments of the invention, an amplification method is provided comprising swarm primers FS, BS and inner primers FIP, BIP without the use of outer primers F3, B3 to displace the FIP or BIP initiated strand formed from the target strand. Rather, swarm primers FS, BS are used to split the double-stranded amplicons formed during the process. This may be useful because it may be difficult for particular target templates to find optimal binding sites for the outer primers F3, B3. Reference is made to FIGS. 7A to 7J, illustrating one example of a chain of reactions that may occur. As shown, FIGS. 7A to 7B illustrate the same initial steps as shown in FIGS. 3A to 3D. The difference occurs in FIG. 7C, wherein a second swarm primer B1S is used to split the double-stranded amplicon 101, rather than an outer primer. Each time a swarm primer is introduced, a partially double-stranded amplicon results 102, 122, 132, 141 as well as a double-stranded amplicon 101, 121, 124, 135. In the embodiment shown, first double-stranded amplicon 101 leads to second double-stranded amplicon 121 which leads to a stem-loop amplicon 200. Likewise, third double-stranded amplicon 124 leads to fourth double-stranded amplicon 135 which leads to a dumbbell amplicon 70. As explained above, dumbbell amplicons become stem-loop amplicons in LAMP cycling. As illustrated, the cycle repeats continuously, thus continuously creating stem-loop amplicons for LAMP cycling without utilizing any outer primers F3, B3.

Whereas the embodiments described above are generally directed to one swarm primer F1S or B1S reacting with the sample DNA or amplicon, one of ordinary skill in the art will understand that both F1S and B1S may react on the same piece of DNA or amplicon without deviating from the scope of the invention. For example, FIGS. 8A-8D illustrate an exemplary chain of reactions wherein both F1S and B1S anneal to the same original double-stranded DNA sample as well as to the double-stranded amplicons formed thereafter. As shown, such a reaction quickly produces stem-loop amplicons 200, 220 as well as double-stranded amplicons 201, 202, 211, 212 which are further split and from which more stem-loop amplicons 200, 220 and double-stranded amplicons 201, 202, 211, 212 are formed at an exponential rate. Another type of amplicon formed in high volume is the swarm amplicon 302, 304, 306, 308.

Figure 9A:
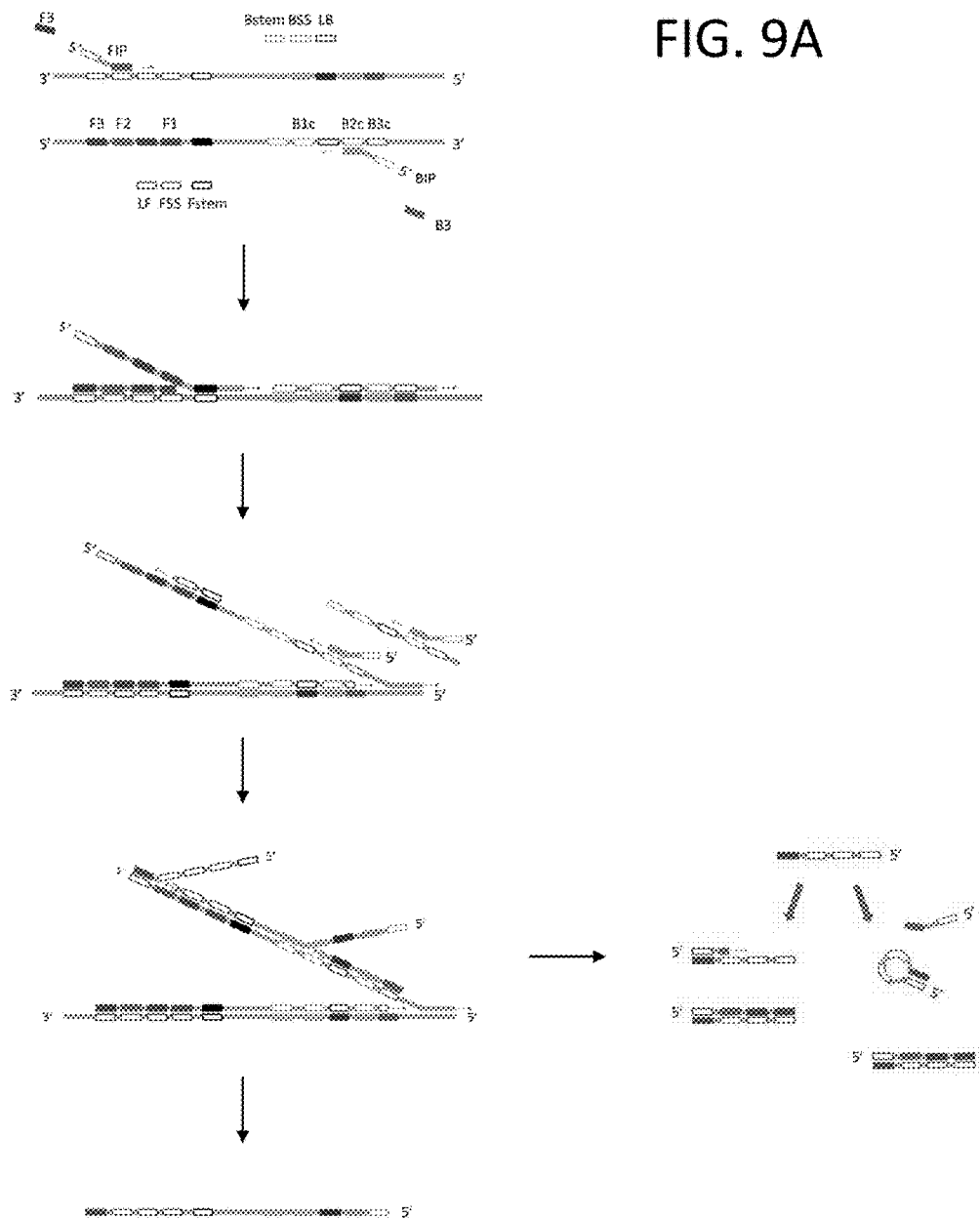
FIG. 9A is an illustration of parts of the reaction principle in accordance with another embodiment of the invention.
Figure 9B:
FIG. 9B is an illustration of parts of the reaction principle of the embodiment of FIG. 9A.
Figure 1:
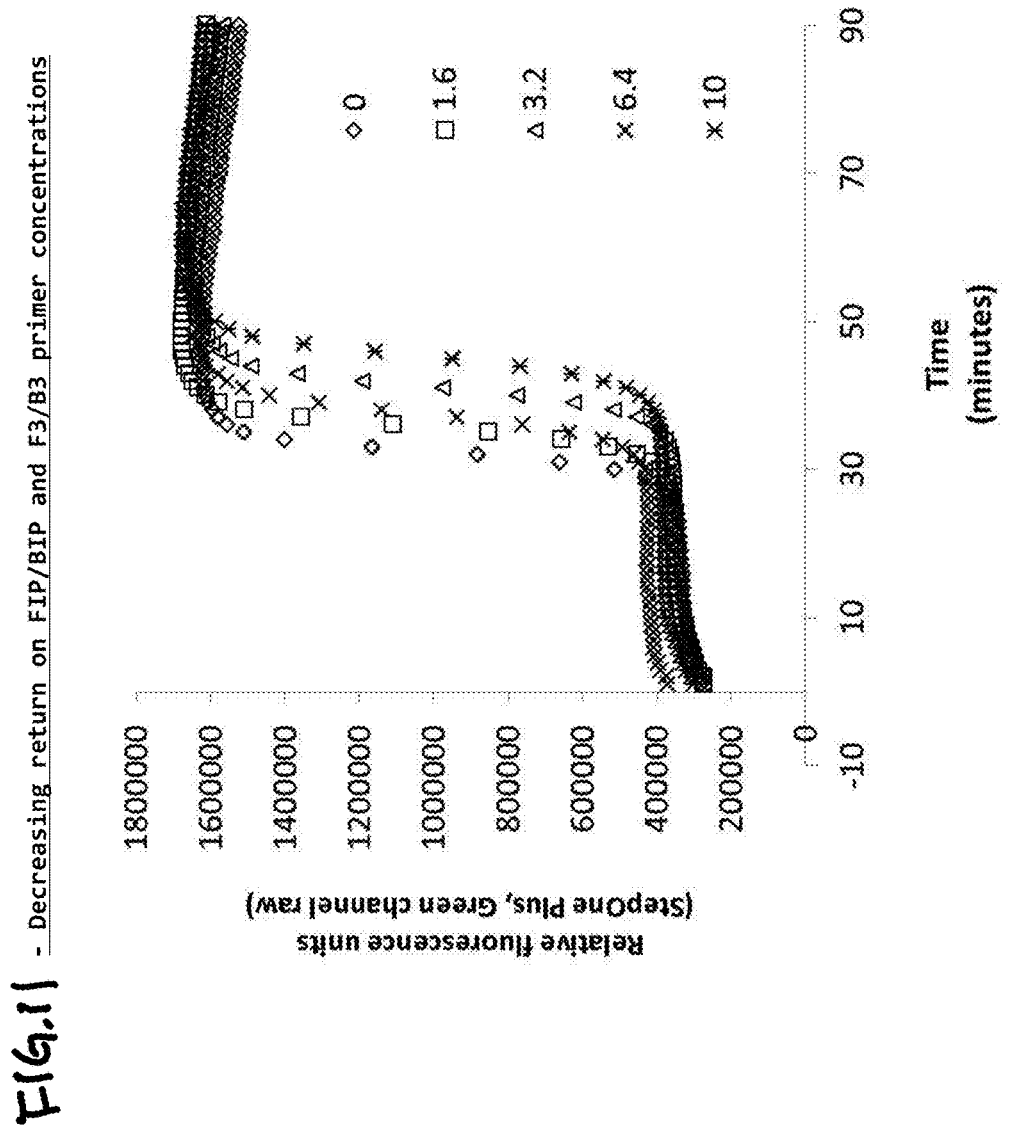
Figure 14:
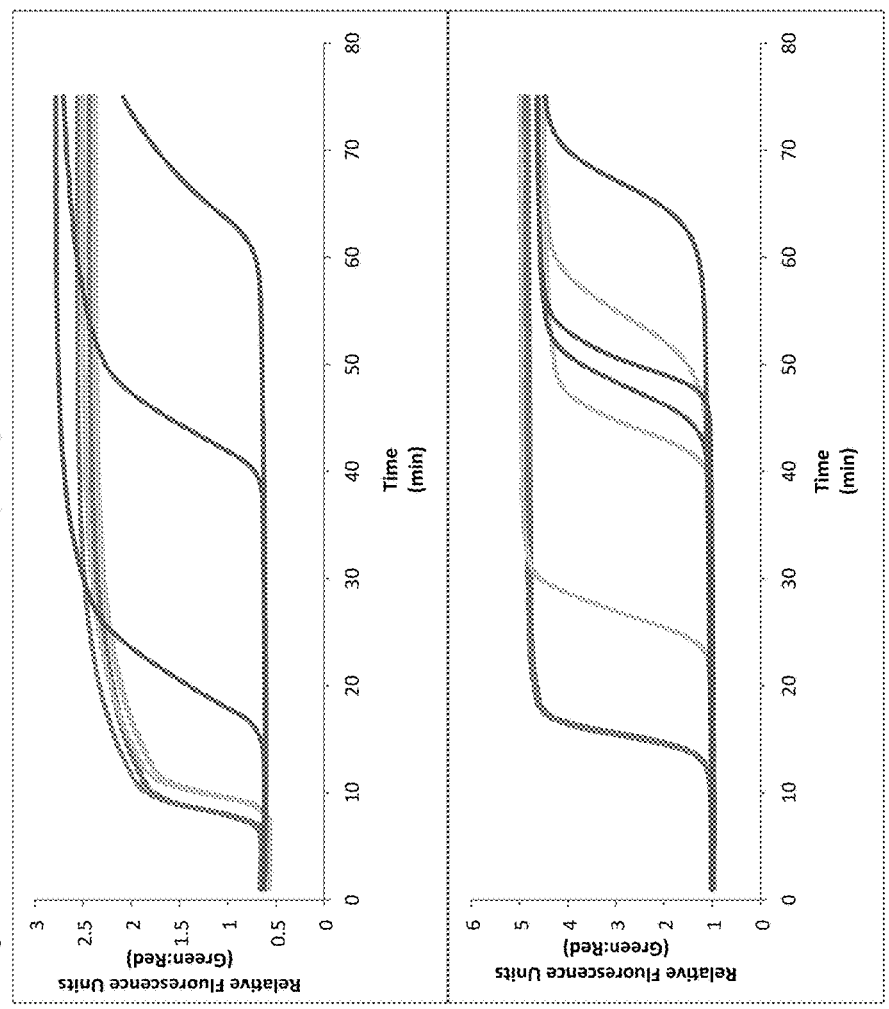
FIG. 14 is an illustration of exemplary effects of including various primer sets on the analytical performance.
Figure 15:
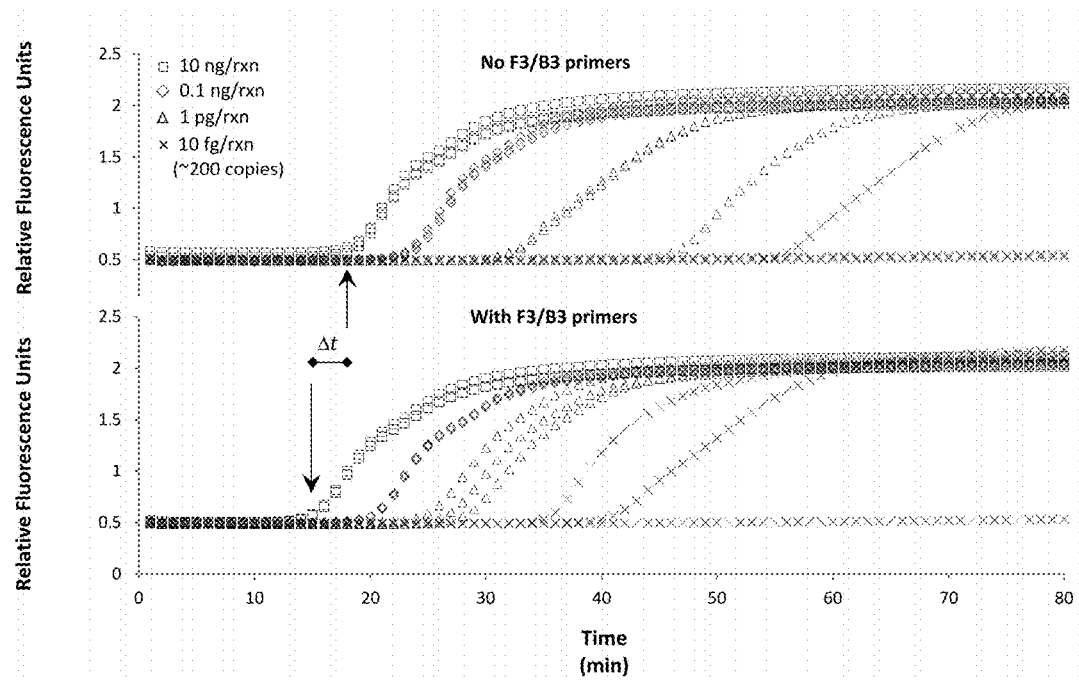
FIG. 15 is an illustration of exemplary effects of including various primer sets on the analytical performance.
Figure 16:
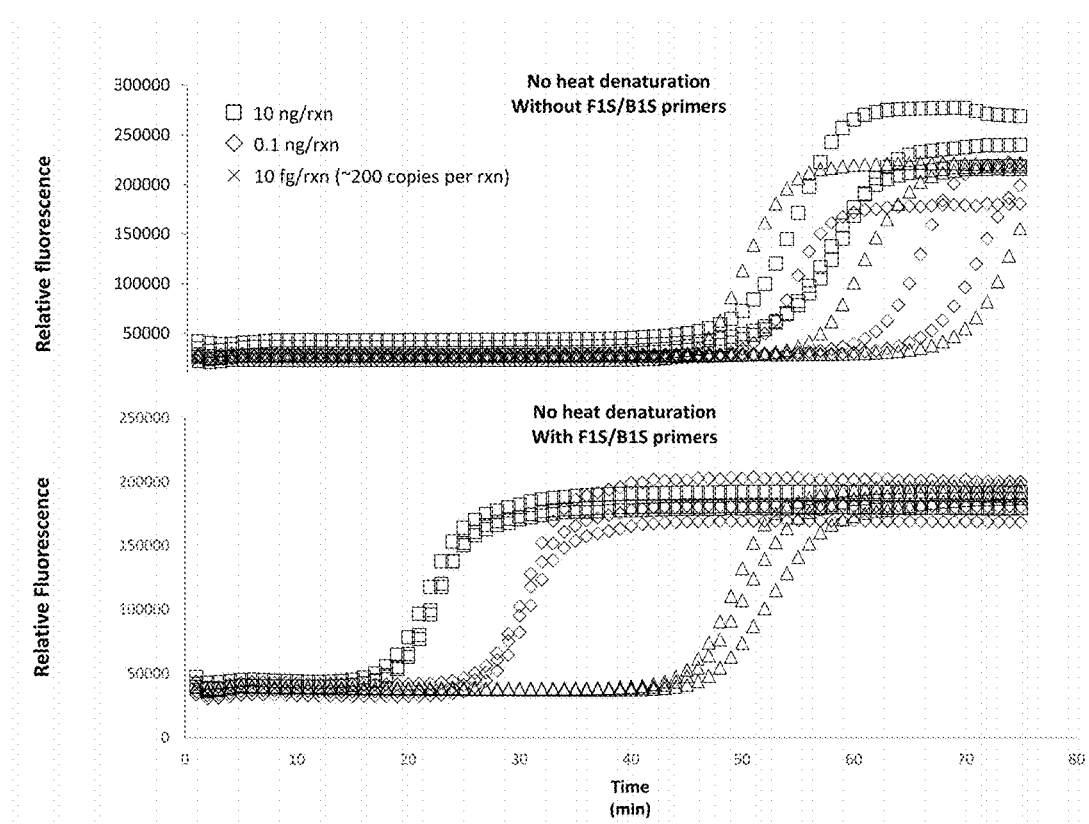
FIG. 16 is an illustration of exemplary effects of including various primer sets on the analytical performance.
Figure 17:
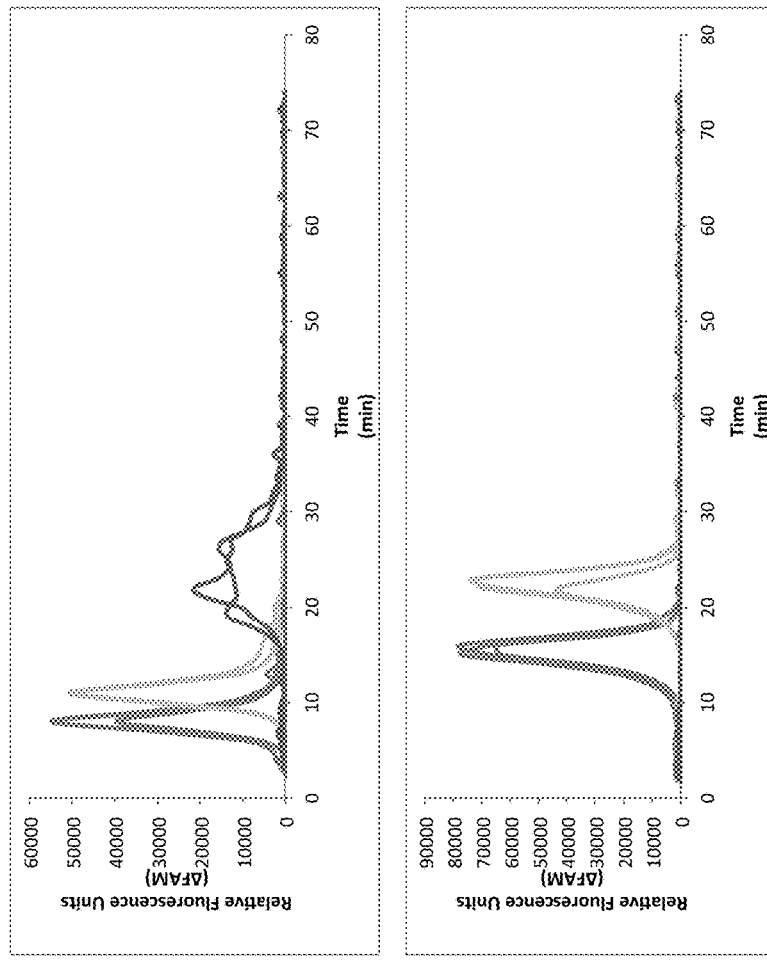
FIG. 17 is an illustration of exemplary effects of including various primer sets on the analytical performance.

Swarm amplicons are formed in each of the examples described herein. They may be single-strand or double-strand. Generally, when a single-strand swarm amplicon is created, an inner primer FIP, BIP will anneal to the single-strand swarm amplicon to create a double-strand swarm amplicon. Reference is made to FIGS. 9A-9B, which illustrate certain embodiments wherein swarm amplicons are created. Whereas these swarm amplicons do not participate in amplifying the target DNA, they may increase the amount of signal produced to improve detection, and may also downstream sequencing operations.

Furthermore, whereas certain exemplary reactions are depicted and described herein, it is to be understood that other reactions between the primers described and the amplicons or sample DNA are expected.

Test Results

The experimental results support the finding that utilizing swarm primers generally increases the rate of DNA amplification compared to LAMP. This result is consistent with both heat denatured templates and templates for which heat denaturation was not performed. First, LAMP requires pre-amplification heat or chemical denaturation which may be beneficial for some templates while damaging for others. For certain templates for which heat denaturation is undesirable, swarm primers may be desirable because they may separate the DNA strands without the use of high heat. Additionally, LAMP has moderate reaction variability, which increases with lower template concentration reactions. The embodiments of the invention described herein can take a single DNA sample and generate duplicates thereof and utilize each of those duplicates in generating more duplicates and amplicons for LAMP cycling, as well as produce more amplicons for LAMP cycling from each DNA sample, in contrast to the traditional LAMP method. Therefore, the method in accordance with certain embodiments of the invention is not as affected by lower template concentration. LAMP also has moderate reaction speed, which may be improved upon by the invention as described herein. Moreover, whereas the results are generally detectable by the naked eye, LAMP provides relatively weak color/turbidity changes. The invention as described remedies that shortcoming as well with the volume of swarm amplicons produced, as described herein.

Therefore, embodiments of this invention may be useful in portable and/or resource-constrained genetic analysis locations or equipment by improving portability, reducing cost and improving function of genetic analyzers. The embodiments of the invention described may be used in: water analysis kits, environmental samplers, virus/bacteria screenings for human health, aqua culture, and many other DNA analyzers where low cost, lower-power, highly distributed or potentially disposable instruments are desirable.

LAMP and other previously available methods and scholarly reports thereon teach away from annealing a primer in the sites used for amplification in the embodiments of the invention described. These sites are not expected to participate in amplification elongation because there are reportedly no single-stranded building sites available. However, embodiments of the invention described herein provides primers in those unexpected sites and separate the DNA strands to expose sites for the inner primers, loop primers, and/or stem primers to anneal to. Positioning primers in areas suspected to be double-stranded has not been taught, but rather, taught against, and thus the use of swarm primers in such areas is novel, both when used with FIP, BIP as well as with other accessory primers.

Additionally, LAMP teaches away from using too high a concentration of primers. The LAMP inventors, through trial and error, recommended a certain primer concentration (1.6 micromolar for each of FIP/BIP, for example). A higher concentration not only does not improve performance, it was observed to lead to performance deterioration. In contrast, in embodiments of the invention described herein, concentrations of swarm primers greater than the greatest standard LAMP primer concentration were shown to have improved results, and are preferred. For example, the inventors observed improved results from using up to 10 μM primer concentrations.

Lesser effects were observed at lower concentrations, but the addition of the swarm primers in general had positive effects on the reactions. FIG. 10 illustrates an example of the increasing effect of swarm primers on reaction speed. For certain primer sets, higher concentrations of swarm primers may have better results. In contrast, simply increasing FIP/BIP or F3/B3 primer concentrations over standard published optimized values may result in decreasing returns, as shown in FIG. 11. FIG. 12 illustrates an example of the analytical performance increases associated with using swarm primers, as tracked using the intercalating dye EvaG. Performance increases include increased reaction rate and decreased variability.

However, for dye systems that report on the total amount of dNTPs (deoxynucleotides) integrated into growing products, e. g. hydroxynaphthol blue (HNB), Calcein, and pH indicator dyes, another benefit of adding Swarm primers can total signal is increased. As seen in gel runs, adding Swarm primers may produce both new amplicons and a greater amount of amplicons, both single and double-stranded (although the gel typically cannot distinguish between the two). When indicators act by reporting the total amount of dNTPs incorporated, Swarm priming may increase signal production due to increases in both single and double-stranded DNA products. Thus, even for templates that might be prone to increased single-stranded DNA production (at the expense of double-stranded DNA production), this may still translate into increased signal production. FIG. 13A illustrates the increased signal production as a result of the addition of swarm primers to the HNB reaction. FIG. 13B illustrates an example of reduced variability associated with swarm primers. The optimal swarm primer concentration may depend not only on the given primer set and target performance characteristics, but also on the type of indicator dye used to monitor the system. For the primer sets and targets used in the example, a swarm primer concentration approximately double that of the maximum used in conventional LAMP, i.e. approximately 3.2 µM swarm primers F1S, B1 S, seems to offer optimal performance and may be preferred.

Using the new primers with the standard primer concentrations, either using 4 primers or 6 primers, provided improved results compared to both heat-denatured Lambda phage DNA template and non-denatured Lambda phage DNA template under standard LAMP reaction conditions. The figures illustrate examples of performance improvements achieved when using swarm primers instead of heat-denaturation. In all the cases observed here, there are performance increases when swarm primers are added to LAMP reactions.

Favorable results are also obtained when sets of original LAMP primers, F3/B3 or LF/LB, are omitted. The following primer sets are effective to various degrees: 4 primers (FIP/BIP and F1S/B1S), 6 primers (FIP/BIP, F1S/B1S and F3/B3), 6 primers (FIP/BIP, F1S/B1S and LF/LB), and 8 primers (FIP/BIP, F1S/B1S, F3/B3 and LF/LB). The best performance among the tested samples is achieved with the 8 primers set. FIGS. 14-17 illustrate the effects of including various primer sets on the analytical performance. Preferably, the FIP/BIP primers are provided for the chain reaction in accordance with the invention, while displacement primers F3/B3 are optional with the use of swarm primers.

Whereas the swarm primers have been described herein with respect to LAMP, it is to be understood that the swarm primers may be used in any isothermal amplification technique.

The swarm primers F1S, B1S described herein preferably are a forward swarm primer in the F1 region and a backward swarm primer in the B1 region, respectively. Each is preferably designed to anneal to the double-stranded DNA 5-50 base pairs downstream of the FIP/BIP primer target region but on the opposite strand. Most preferably, the swarm primer F1S, B1S is designed to significantly overlap the F1 and B1 region, respectively.

Figure 19:
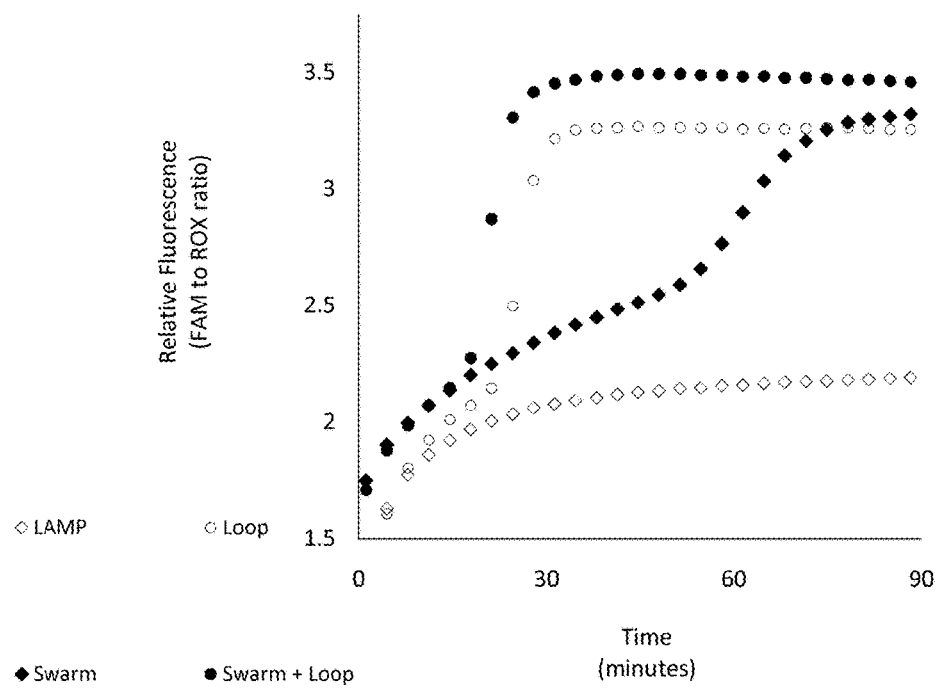
FIG. 19 shows an exemplary test result comparing relative fluorescence of LAMP, LAMP with swarm primers, LAMP with loop primers, and LAMP with loop primers and swarm primers.

The swarm primers are generally 8-30 bases long, more preferably between 15 and 25. A schematic example of LAMP in the presence of swarm primers is provided in FIG. 18. As shown, swarm primers F1S, B1S bound to their recognition sites and initiated polymerase extension, causing the double-stranded DNA to open up. Thus, the FIP, BIP, F3, B3 recognition sites became exposed, to which the inner primers FIP, BIP and outer primers F3, B3 annealed. Therefore, the reaction kinetics for FIP, BIP, F3, B3 primer binding and extension are improved, resulting in improved performance. FIG. 19 shows an exemplary test result comparing relative fluorescence of LAMP, LAMP with swarm primers, LAMP with loop primers, and LAMP with loop primers and swarm primers. As the graph shows, in the example illustrated, adding swarm primers improved reaction initiation.

FIG. 20 shows the result of LAMP reactions with or without F1S/B1S swarm primers, run on DNA 1000 chips. The assays contained internal double-strand DNA standards of 15 and 1500 bps. The most significant peaks are annotated with their estimated fragment lengths. Panel A shows the results of running a 4-primer reaction, in which numerous peaks are visible between 15 and 1500 bps, and three amplicons near 200 bps are noted with putative structures. There are peaks with sizes less than 50 bps, which may be primers. There appear to be no substantial amplicons with sizes between 50 and 150 bps. However, when a 4-primer reaction is supplemented with F1S/B1S swarm primers (Panel B), additional peaks are observed. Four distinct peaks are apparent in the 50-150 bps range, possibly corresponding to 4 possibly new amplicon species. The indicated species run sizes are estimates. FIG. 20 also shows new peaks manifesting near the 200 and 300 bp markers.

FIG. 21 illustrates graphs indicating examples of the superpositioning of LAMP amplicon products when two sets of primers are used. Panel A repeats an earlier presentation of the 4-primer plus swarm treatment results, whereby 4 amplicons are produced in the 50-150 bp range. Panel B shows the amplicons produced when the 4-primer LAMP is supplemented with loop primers, in which two new amplicons are produced. When both primer sets are added concurrently to a reaction (Panel C), 6 peaks are visible in the 50-150 size range, agreeing qualitatively with mapping estimates and may indicate that all species are being produced in parallel.

The swarm primers may be designed using methods used for designing LAMP primers, for example, the various software programs available. As mentioned above, the swarm primers F1S, B1S preferably significantly overlap sites F1, B1, and therefore, in accordance with an embodiment of the invention, F1c, B1c of the inner primers FIP, BIP may be used as a reference for designing the swarm primers F1S, B1S.

Other alterations may be made without deviating from the scope of the invention. Accordingly, the system and method, the use, steps, order of steps, etc. may be varied as a matter of application specific design choice without deviating from the scope of the invention. It is the intention, therefore, to be limited only as indicated by the scope of the claims appended hereto. For example, swarm primers F1S, B1S may anneal to a corresponding F1, B1 site on a single-stranded DNA, a single or double-stranded loop.

It is also to be understood that the following claims are intended to cover all of the generic and specific features of the invention herein described and all statements of the scope of the invention which, as a matter of language, might be said to fall there between.

We claim:

1. A method of synthesizing a nucleic acid complementary to a target nucleic acid sequence in a template nucleic acid, the method comprising:
   providing a target nucleic acid having a 5' side having an F1 site and an F2 site, and a 3' side having a B1C site and a B2C site;
   annealing a swarm primer to said target nucleic acid, wherein said swarm primer overlaps said F1 site;
   initiating polymerase extension of said swarm primer toward said F2 site; and
   conducting a loop-mediated isothermal amplification of said target nucleic acid.

2. The method of claim 1, wherein said target nucleic acid comprises a first loop at said 5' side wherein said 5' side includes an F1C site complementary to and annealing to said F1 site to form said first loop.

3. The method of claim 1, wherein said target nucleic acid comprises a second loop at said 3' side wherein said 3' includes a B1 site complementary to and annealing to said B1C site to form said second loop.

4. The method of claim 2, further comprising annealing a first loop primer to said first loop and extending said first loop primer.

5. The method of claim 3, further comprising annealing a second loop primer to said second loop and extending said second loop primer.

6. The method of claim 1, wherein said swarm primer is an oligonucleotide primer.

7. The method of claim 1, further comprising annealing a first inner primer to said B2C site, said first inner primer substantially overlapping said B2C site, and extending said inner primer toward said B1C site.

8. The method of claim 1, further comprising annealing a second swarm primer onto a second 5' side of said target nucleic acid, said second 5' side having a B1 site and B2 site, wherein said second swarm primer substantially overlaps said B1 site.

9. The method of claim 1, further comprising annealing a displacement primer to a B3C site of said target nucleic acid, and extending said displacement primer toward said B2C site.

10. The method of claim 1, wherein said target nucleic acid comprises one or more single-stranded loops.

11. The method of claim 10, further comprising annealing a stem primer to said single-stranded loop.

12. The method of claim 1, further comprising reproducing a plurality of single-strand loop amplicons.

13. The method of claim 12, further comprising repeatedly reproducing at least one of said single-stranded loop amplicons.

14. The method of claim 10, further comprising reproducing a plurality of stem-loop amplicons.

15. The method of claim 1, further comprising reproducing a plurality of double-stranded amplicons.

16. The method of claim 1, further comprising reproducing a plurality of double-loop amplicons.

17. The method of claim 1, further comprising reproducing a plurality of swarm amplicons.

18. The method of claim 1, further comprising conducting a strand displacement reaction.

19. A method of synthesizing a nucleic acid complementary to a target nucleic acid sequence in a template nucleic acid, the method comprising:
   providing a target nucleic acid having a 5' side having an F1 site and an F2 site, and a 3' side having a B1C site and a B2C site;
   annealing a swarm primer to said target nucleic acid, wherein said swarm primer overlaps said F1 site;
   initiating polymerase extension of said swarm primer toward said F2 site;
   annealing a first inner primer having a primer B2 site and a primer B1C site to said target nucleic acid, wherein said inner primer overlaps said B2C site;
   initiating polymerase extension of said first inner primer toward said B1C site of said target nucleic acid and synthesizing a complementary nucleic acid comprising a complementary sequence of said target nucleic acid;
   conducting a strand displacement reaction to displace said complementary nucleic acid from said target nucleic acid.

20. A method of synthesizing a nucleic acid complementary to a target nucleic acid sequence in a template nucleic acid, the method comprising:
   providing a target nucleic acid having a 5' side having an F1 site and an F2 site, and a 3' side having a B1C site and a B2C site;
   annealing a swarm primer to said target nucleic acid, wherein said swarm primer substantially overlaps said F1 site;

initiating polymerase extension of said swarm primer toward said F2 site;
annealing a first inner primer having a primer B2 site and a primer B1C site to said target nucleic acid, wherein said inner primer substantially overlaps said B2C site;
initiating polymerase extension of said first inner primer toward said B1C site of said target nucleic acid and synthesizing a complementary nucleic acid comprising a complementary sequence of said target nucleic acid;
synthesizing a single-loop amplicon;
annealing a second inner primer to said single-loop amplicon;
initiating polymerase extension of said second inner primer and synthesizing a second complementary nucleic acid comprising a complementary sequence of said single-loop amplicon;
conducting a strand displacement reaction to displace said second complementary nucleic acid from said single-loop amplicon.

* * * * *

SEQUENCE LISTING

<160> NUMBER OF SEQ ID NOS: 1

<210> SEQ ID NO 1
<211> LENGTH: 330
<212> TYPE: DNA
<213> ORGANISM: Homo sapiens

<400> SEQUENCE: 1

```
attttcggtg cgagtatccg taccattcag aactggcagg aacagggaat gcccgttctg      60
cgaggcggtg gcaagggtaa tgaggtgctt tatgactctg ccgccgtcat aaaatggtat     120
gccgaaaggg atgctgaaat tgagaacgaa aagctgcgcc gggaggttga agaactgcgg     180
caggccagcg aggcagatct ccagccagga actattgagt acgaacgcca tcgacttacg     240
cgtgcgcagg ccgacgcaca ggaactgaag aatgccagag actccgctga agtggtggaa     300
accgcattct gtactttcgt gctgtcgcgg                                      330
```